(12) United States Patent
Federspiel et al.

(10) Patent No.: US 11,013,545 B2
(45) Date of Patent: May 25, 2021

(54) DISTRACTION/COMPRESSION APPARATUS AND METHOD FOR BONE

(71) Applicant: Acumed LLC, Hillsboro, OR (US)

(72) Inventors: Joshua Paul Federspiel, Portland, OR (US); David William VanVleet, Hillsboro, OR (US)

(73) Assignee: Acumed LLC, Hillsboro, OR (US)

( * ) Notice: Subject to any disclaimer, the term of this patent is extended or adjusted under 35 U.S.C. 154(b) by 366 days.

(21) Appl. No.: 15/993,341

(22) Filed: May 30, 2018

(65) Prior Publication Data

US 2019/0365444 A1 Dec. 5, 2019

(51) Int. Cl.
*A61B 17/88* (2006.01)
*A61B 17/00* (2006.01)

(52) U.S. Cl.
CPC .. *A61B 17/885* (2013.01); *A61B 2017/00477* (2013.01)

(58) Field of Classification Search
CPC ....... A61B 17/885; A61B 17/60; A61B 17/66; A61B 17/681
USPC ....................................................... 606/105
See application file for complete search history.

(56) References Cited

U.S. PATENT DOCUMENTS

| | | |
|---|---|---|
| 4,187,841 A | 2/1980 | Knutson |
| 4,628,922 A | 12/1986 | Dewar |
| 4,644,943 A | 2/1987 | Thompson et al. |
| 4,978,348 A | 12/1990 | Ilizarov |
| 5,393,161 A | 2/1995 | Mata et al. |
| 5,397,322 A | 3/1995 | Campopiano |
| 5,439,465 A | 8/1995 | Tumibay |
| 5,496,319 A | 3/1996 | Allard et al. |
| 5,591,164 A | 1/1997 | Nazre et al. |
| 5,601,551 A | 2/1997 | Taylor et al. |

(Continued)

FOREIGN PATENT DOCUMENTS

| | | |
|---|---|---|
| CN | 104434282 A | 3/2015 |
| EP | 1567064 B1 | 5/2012 |

(Continued)

OTHER PUBLICATIONS

AO Foundation, "Reduction of the metaphysis/diaphysis", accessed Jan. 15, 2018, Distal femur—AO Surgery Reference, 1 page.

(Continued)

*Primary Examiner* — Si Ming Ku
(74) *Attorney, Agent, or Firm* — K&L Gates LLP

(57) ABSTRACT

Apparatus and methods for distracting and/or compressing bone. An exemplary apparatus may comprise a rod having a thread. The apparatus also may comprise a first assembly and a second assembly each coupled, or configured to be coupled, to the rod and each configured to be attached to a respective pin extending into bone. The apparatus further may comprise a nut engaged, or configured to be engaged, with the thread and configured to be turned to drive the second assembly along the rod. In some embodiments, at least one of the assemblies may have at least two degrees of rotational freedom that can be eliminated by manipulating a single graspable member. In some embodiments, the rod and the second assembly may have anti-rotation features configured to interact with one another to permit travel of the second assembly along the rod while preventing rotation of the second assembly about the rod.

19 Claims, 10 Drawing Sheets

(56) References Cited

U.S. PATENT DOCUMENTS

| | | |
|---|---|---|
| 5,662,649 A | 9/1997 | Huebner |
| 5,662,650 A | 9/1997 | Bailey et al. |
| 5,676,664 A | 10/1997 | Allard et al. |
| 5,707,370 A | 1/1998 | Berki et al. |
| 5,709,681 A | 1/1998 | Pennig |
| 5,743,898 A | 4/1998 | Bailey et al. |
| 5,752,954 A | 5/1998 | Mata et al. |
| 6,007,535 A | 12/1999 | Rayhack et al. |
| 6,056,748 A | 5/2000 | Weiner |
| 6,217,577 B1 | 4/2001 | Hofmann |
| 6,277,119 B1 | 8/2001 | Walulik et al. |
| 6,328,737 B1 | 12/2001 | Moorcroft et al. |
| 6,746,448 B2 | 6/2004 | Weiner et al. |
| 7,311,711 B2 | 12/2007 | Cole |
| 7,479,142 B2 | 1/2009 | Weiner et al. |
| 8,211,106 B2 | 7/2012 | Labbe et al. |
| 8,419,732 B2 | 4/2013 | Mullaney |
| 8,758,343 B2 | 6/2014 | Maughan et al. |
| 8,808,176 B2 | 8/2014 | Menendez et al. |
| 9,539,029 B1 | 1/2017 | Muniz et al. |
| 9,622,782 B1 | 4/2017 | Alruhaimi |
| 9,788,861 B2 | 10/2017 | Murray et al. |
| 2004/0133200 A1 | 7/2004 | Ruch et al. |
| 2006/0276786 A1 | 12/2006 | Brinker |
| 2007/0093696 A1 | 4/2007 | Sharratt |
| 2012/0143191 A1 | 6/2012 | Foote |
| 2015/0066088 A1* | 3/2015 | Brinkman .......... A61B 17/7077 606/264 |

FOREIGN PATENT DOCUMENTS

| | | |
|---|---|---|
| EP | 2874551 B1 | 8/2017 |
| WO | 2015137976 A1 | 9/2015 |

OTHER PUBLICATIONS

AO Foundation, "Revised AO/OTA Classification, Femur shaft 32-C3 ORIF subtrochanteric", Journal of Orthopaedic Trauma, Jan. 2018, 13 pages.
Depuy Synthes, "Fracture Reduction and Provisional Stabilization Large Distractor—Tibia", Surgical Technique, May 2017, 22 pages.
Gautier, Emanuel et al, "Reduction Techniques—Traction or Distraction", AO Principles of Fracture Management, accessed Jan. 15, 2018, 4 pages.
Kapruwan Orthopedic, "Femoral Distractor Large", Orthopedic Surgical Instruments Product Overview, (c) 1999-2018, accessed Jan. 15, 20018, 3 pages.
Real Boom Surgical Company, "Femoral Distractor Orthopaedic Medical Surgical Instrument", Orthopedic Surgical Instruments Product Overview, (c) 1999-2018, accessed Jan. 15, 2018, 2 pages.
Copenheaver, Blaine R., Authorized Officer, ISA/US, Commissioner for Patents, "International Search Report" in connection with related International Application No. PCT/US2019/034406, dated Aug. 9, 2019, 5 pgs.
Copenheaver, Blaine R., Authorized Officer, ISA/US, Commissioner for Patents, "Written Opinion of the International Searching Authority" in connection with related International Application No. PCT/US2019/034406, dated Aug. 9, 2019, 10 pgs.

* cited by examiner

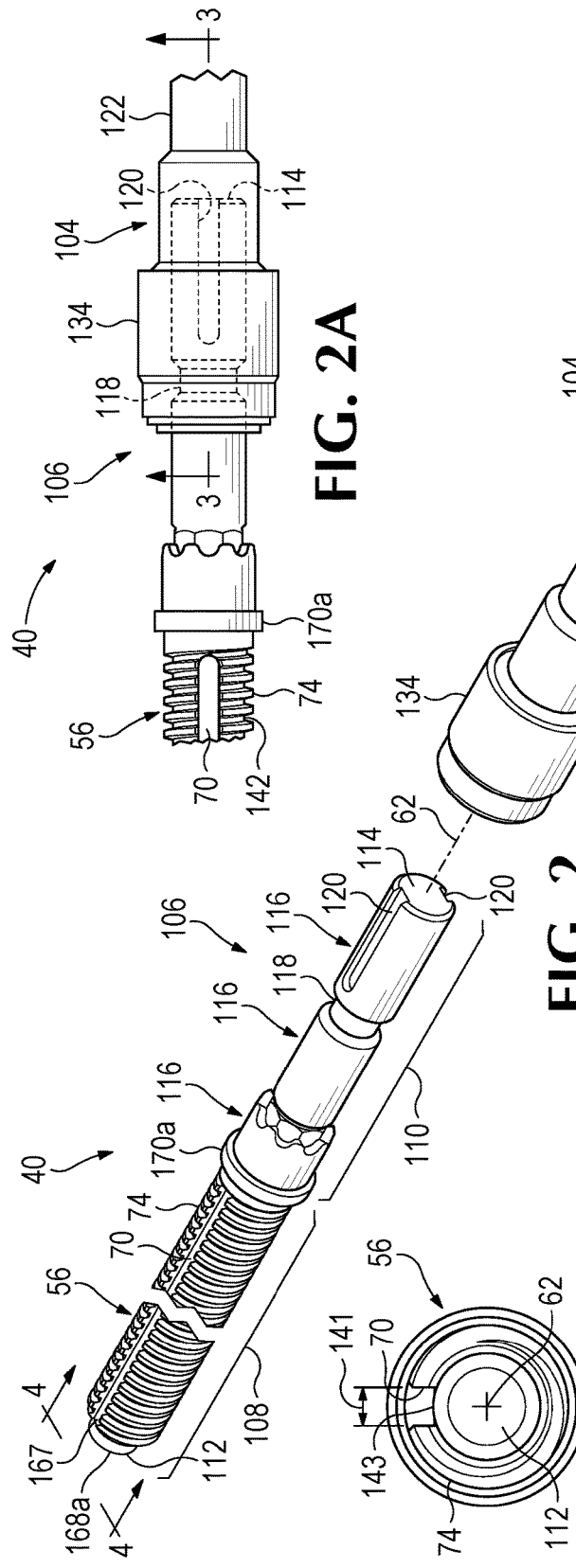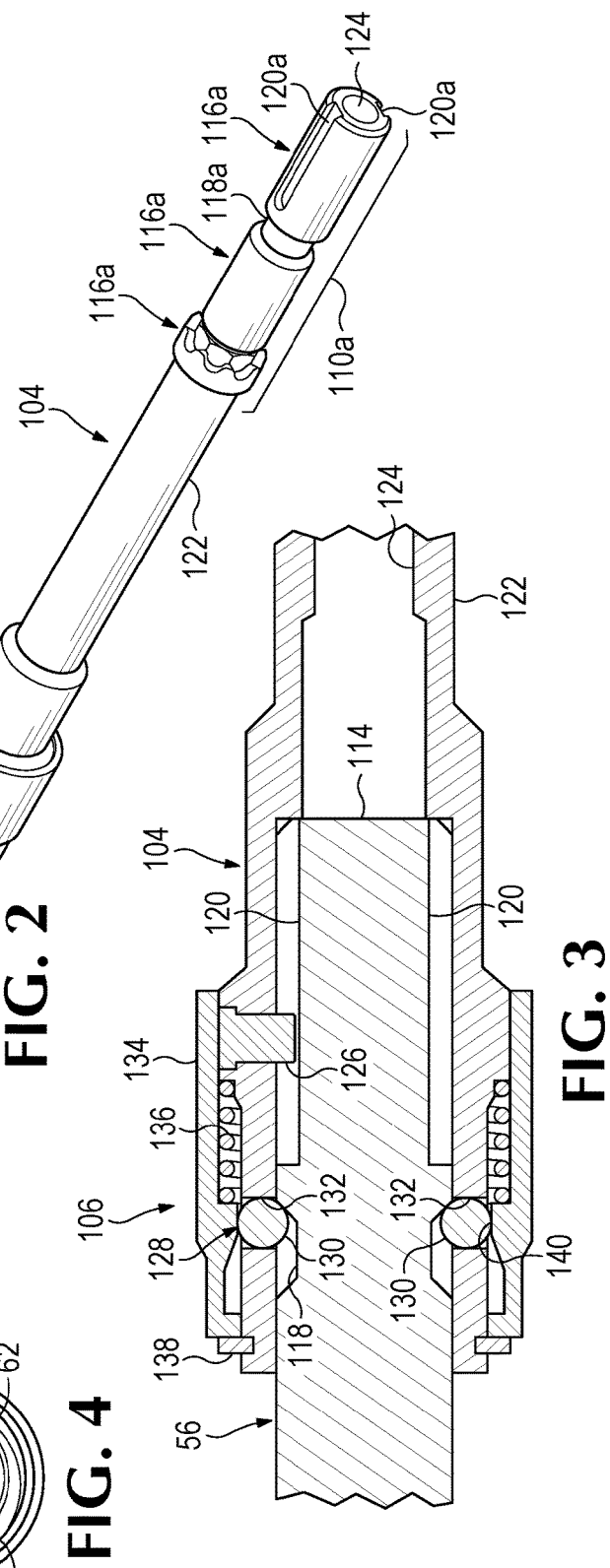

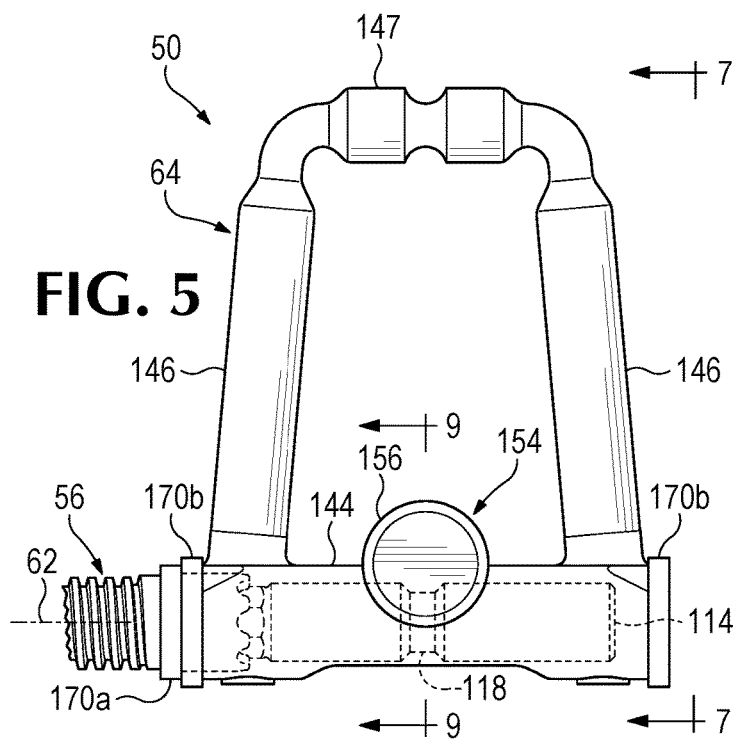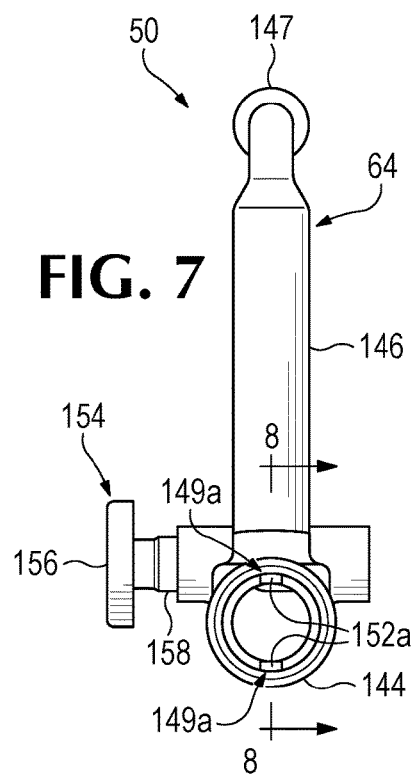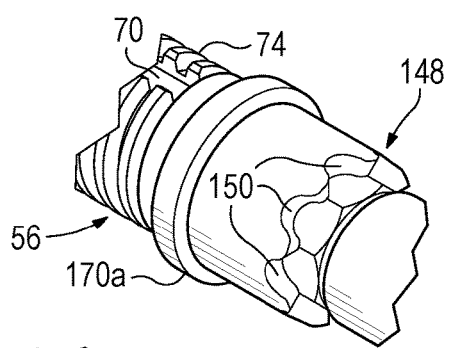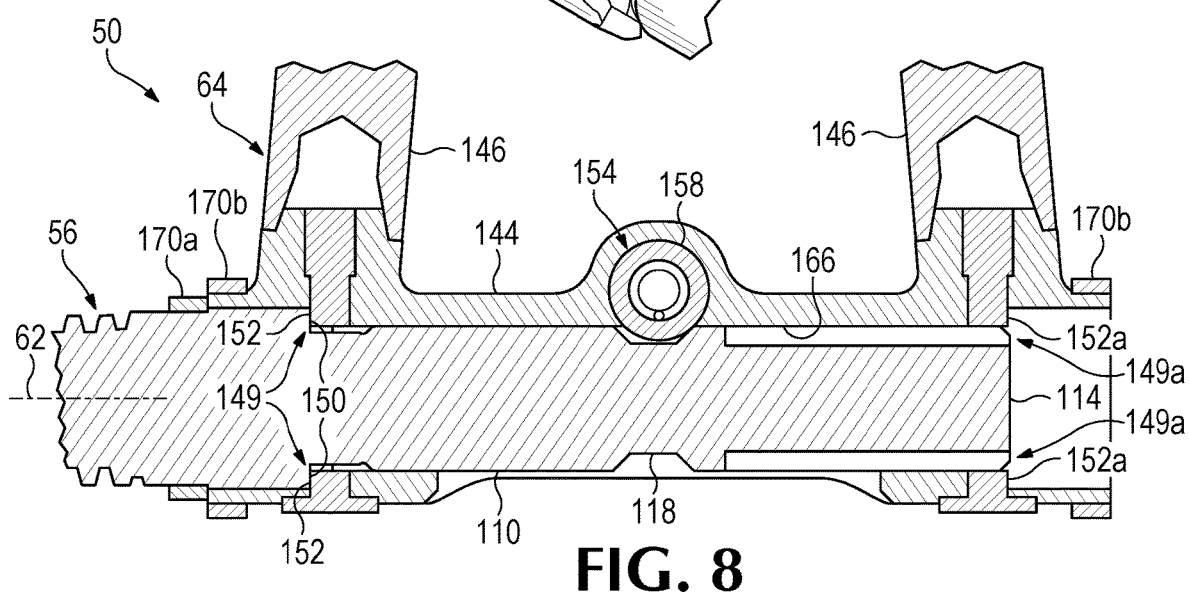

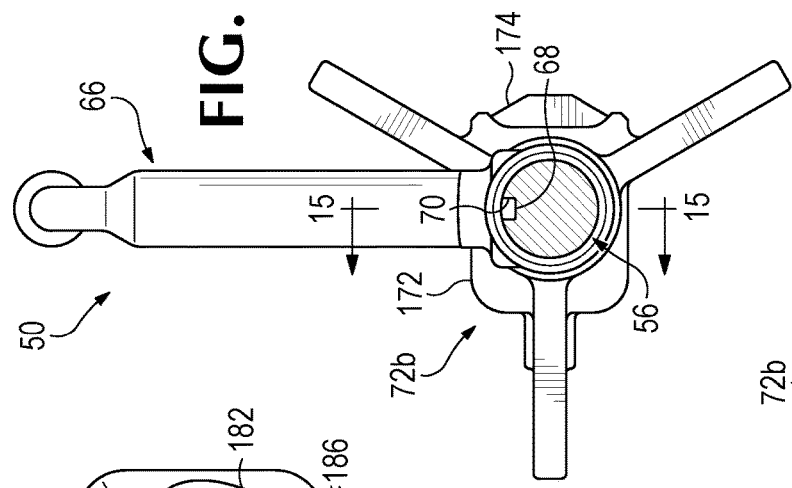
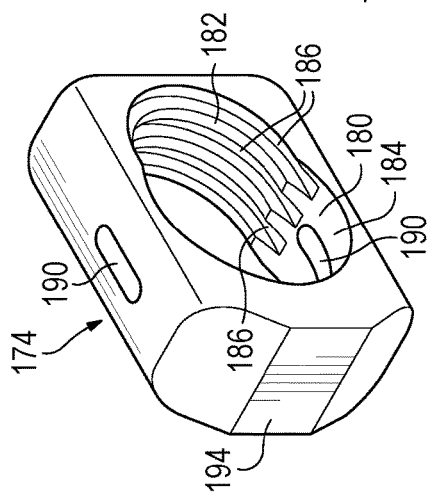
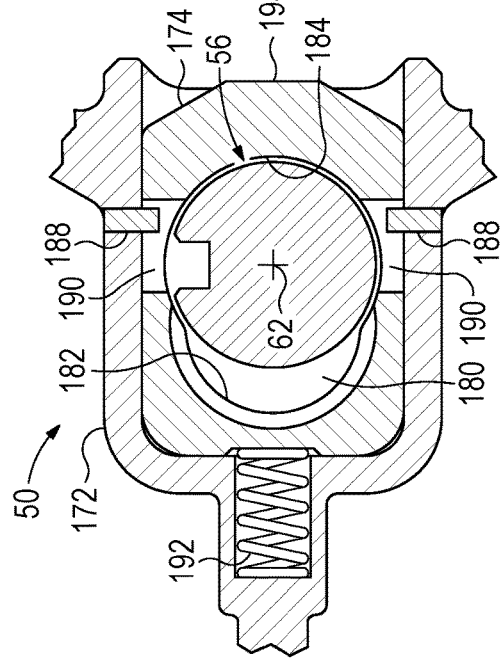
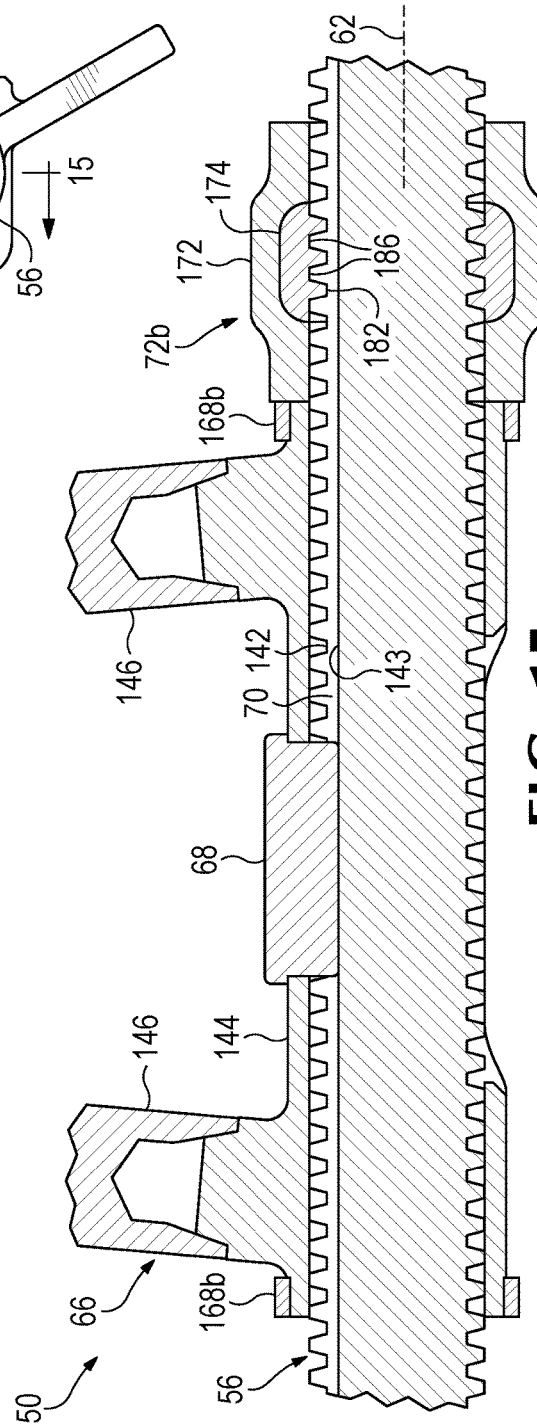

DISTRACTION/COMPRESSION APPARATUS AND METHOD FOR BONE

INTRODUCTION

A long bone, such as the femur, tibia, or humerus, when sufficiently fractured, is often treated by attachment to an implant, such as a plate, nail, screw, or the like. The implant is an internal fixation device introduced surgically to reinforce the bone and keep it aligned during healing.

Soft tissue attached to a fractured bone, particularly a bone of the arm or leg, can axially compress the bone. This compression can hold fragments of the bone in displaced configurations before the bone is fixed. A surgeon may need to overcome this compressive force by applying tensile force to the bone before the fragments can be returned to their anatomical positions and fixed with an implant. A distractor may be used during surgery for this purpose. The distractor can be attached to a pair of pins that have been driven partway into the bone, and then can apply tensile force to the bone through the pins. After reduction of the fracture and fixation of the bone with an implant, the pins and distractor are removed before the surgery is completed.

A widely-used distractor is marketed by DePuy Synthes. This distractor serves its purpose but is not user friendly. Assembly of the distractor in the operating room is laborious. Adjustment of the assembled distractor is inefficient. Taking apart the distractor after surgery is tedious. An improved distractor is needed.

SUMMARY

The present disclosure provides apparatus and methods for distracting and/or compressing bone. An exemplary apparatus may comprise a rod having an external thread. The apparatus also may comprise a first assembly and a second assembly each coupled, or configured to be coupled, to the rod and each configured to be attached to a respective pin extending into bone. The apparatus further may comprise a nut engaged, or configured to be engaged, with the external thread and configured to be turned to drive the second assembly along the rod. In some embodiments, at least one of the assemblies may have at least two degrees of rotational freedom that can be eliminated by manipulating a single graspable member. In some embodiments, the rod and the second assembly may have anti-rotation features configured to interact with one another to permit axial travel of the second assembly along the rod while preventing rotation of the second assembly about the rod.

BRIEF DESCRIPTION OF THE DRAWINGS

FIG. 2 is an exploded view of a rod of the apparatus of FIG. 1 and an exemplary, optional rod extension that mounts coaxially to the rod to form a rod assembly of greater length, in accordance with aspects of the present disclosure.

FIG. 2A is a fragmentary, side view of the rod assembly of FIG. 2, taken generally around the junction between the rod and the rod extension, with the rod extension mounted to the rod.

FIG. 3 is a fragmentary, sectional view of the rod assembly of FIG. 2, taken generally along line 3-3 of FIG. 2A.

FIG. 4 is an end view of the rod of FIG. 2, taken generally along line 4-4 of FIG. 2.

FIG. 5 is a fragmentary, elevation view of selected aspects of the apparatus of FIG. 1, taken around a fixed pin-holding assembly of the apparatus but showing only a stationary base of the pin-holding assembly mounted to an end of the rod.

FIG. 6 is a fragmentary view of the rod of FIG. 2, taken around a mating structure of the rod that fits together with a corresponding mating structure of the stationary base of FIG. 5 in different configurations to permit the user to select a rotational position (and/or radial orientation) of the base from a series of permitted rotational positions (and/or radial orientations).

FIG. 7 is an end view of the stationary base of FIG. 5, taken generally along line 7-7 of FIG. 5.

FIG. 8 is a fragmentary, sectional view of the rod and base of FIG. 5, taken generally along line 8-8 of FIG. 7.

FIG. 12A is another sectional view of the rod, base, and nut of FIG. 10, taken as in FIG. 12, but with the securing member of the nut disengaged from the external thread of the rod.

FIG. 13 is an isometric view of the securing member of the nut of FIGS. 12 and 12A taken in isolation.

FIG. 14 is a sectional view of selected aspects of the apparatus of FIG. 1, taken generally along line 14-14 of FIG. 10.

FIG. 15 is another sectional view of the apparatus of FIG. 1, taken generally along line 15-15 of FIG. 14.

DETAILED DESCRIPTION

Figure 1:
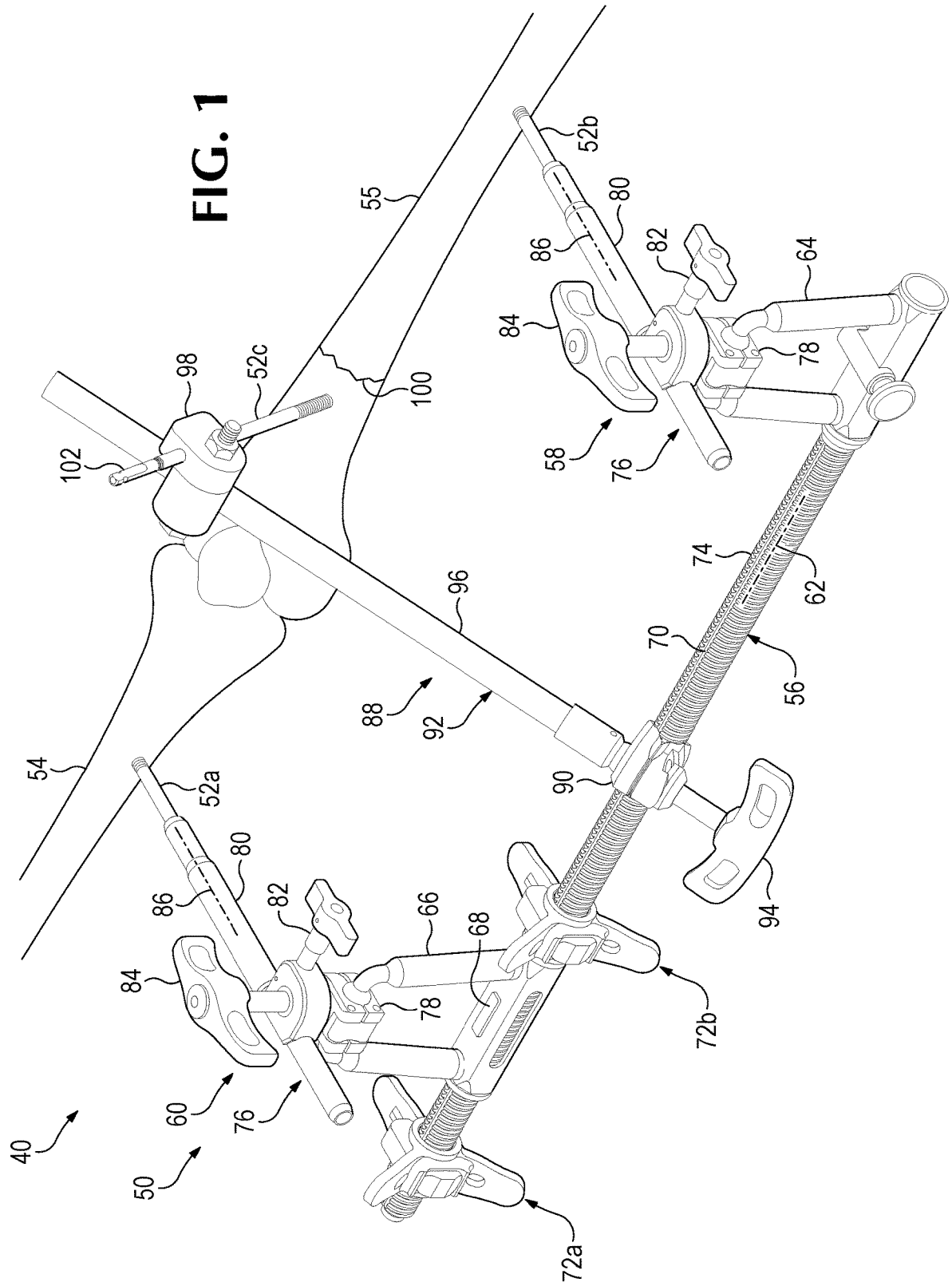
FIG. 1 is a view of an exemplary system including a distraction/compression apparatus attached to a tibia and a fractured femur via a plurality of pins, in accordance with aspects of the present disclosure.

The present disclosure provides apparatus and methods for distracting and/or compressing bone. An exemplary apparatus may comprise a rod having an external thread. The apparatus also may comprise a first assembly and a second assembly each coupled, or configured to be coupled, to the rod, and each configured to be attached to a respective pin extending into bone. The apparatus further may comprise a nut engaged, or configured to be engaged, with the external thread and configured to be turned to drive the second assembly along the rod.

In some embodiments, at least one of the first assembly and the second assembly may include a coupling portion defining a pin-receiving axis and connected to a base that interfaces with the rod. The coupling portion, and/or fastening assembly thereof, may have an adjustable configuration in which an orientation of the pin-receiving axis with respect to the base is adjustable in each plane of a pair of non-parallel planes. The coupling portion and/or the fastening assembly also may have a fixed configuration in which the orientation in each plane of the pair of non-parallel planes is fixed. In some embodiments, the coupling portion and/or the fastening assembly may be configured to be changed between the adjustable configuration and the fixed configuration by moving a single graspable member of the coupling portion and/or fastening assembly. Optionally, the graspable member may be manipulated by rotation, and/or may include one or more wings, such as a pair of wings, projecting in different respective directions from a central body.

In some embodiments, the rod may have at least one anti-rotation feature intersecting the external thread. For example, the at least one anti-rotation feature of the rod may include one or more slots, one or more flats, or a combination thereof, among others. The second assembly may have at least one anti-rotation feature configured to interact with the at least one anti-rotation feature of the rod, to permit axial travel of the second assembly along the rod while preventing rotation of the second assembly about the rod. For example, the anti-rotation feature(s) of the second assembly may include at least one projecting member located, or configured to be located, at least partially in an axial slot of the rod, and/or may include one or more flats for interaction with a corresponding number of axial flats of the rod. The anti-rotation features of the rod and second assembly may rotationally stabilize the second assembly on the rod, without the need for any additional locking action, while permitting the second assembly to move along the rod for distraction/compression of bone.

In some embodiments, the first assembly may include a first base that is pre-attached to the rod (e.g., firmly and/or non-removably attached), or that is configured to be locked to the rod at only one or only a finite plurality of predefined rotational positions (and/or radial orientations) of the first base about a long axis of the rod. In other words, the orientation of the first base may be incrementally adjustable about the rod and/or with respect to a base of the second assembly (a second base). Optionally, the predefined rotational positions (and/or radial orientations) of the first base may be offset from one another by 360/n degrees, with n having an integer value. The radial orientations of the first and second bases relative to one another may be adjusted to be aligned or to have an angular offset that is incrementally adjustable (e.g., by increments of 360/n degrees). Optionally, the first base may include a locking member configured to prevent axial removal of the first base from the rod, such that the first base is locked to the rod. In some embodiments, the locking member may be biased toward a securing configuration, and may be configured to be adjusted, optionally by manual manipulation, to a releasing configuration that permits axial removal of the first base from the rod and/or rotation of the first base to a different one of the rotational positions and/or radial orientations. In some embodiments, the locking member may include a button that can be pushed to unlock the first base from the rod, to permit the orientation of the first base to be adjusted incrementally. Optionally, the second base may be slidably coupled, or configured to be slidably coupled, to the rod at a predefined rotational position (and/or radial orientation) matching one of the predefined rotational positions for the first base. In some embodiments, the predefined rotational position (and/or radial orientation) of the second base may be established by interacting anti-rotation features of the rod and the second assembly.

In some embodiments, the nut may include a body and a securing member coupled to one another. The securing member may be movable with respect to the body between a deployed configuration for engagement with the thread of the rod and a retracted configuration that permits the nut to slide along the rod over the external thread. The nut can be quickly coupled to the rod and/or slid axially on the rod to a desired position along the rod when the securing member is in the retracted configuration. In some embodiments, the nut may be disengaged from the external thread of the rod and re-engaged by respectively pressing and releasing a user interface (e.g., a button structure) of the securing member.

In some embodiments, the nut and the rod may have, or be configured to have, a low-friction threaded coupling with one another when the nut is not under axial load (e.g., when the nut is not exerting pressure on the second assembly). This low-friction coupling may allow the nut to spin easily on the rod, to provide rapid, threaded travel of the nut along a threaded portion of the rod with minimal user effort. For example, the nut may have one or more wings (such as at least two or at least three wings), any of which can be flicked with the user's hand (e.g., a finger thereof) to cause the nut to spin about the rod. The nut may have no parts configured to move relative to one another, or may, for example, include a body and a securing member as described elsewhere herein.

In some embodiments, the apparatus may comprise a third assembly including a clamp configured to mount the third assembly to the rod. The clamp may have jaws configured to engage the external thread of the rod such that the clamp is locked to the rod. The jaws may form a mouth that is adjustable to be larger than a diameter of the external thread, such that a section of the rod can be placed between the jaws by moving the rod and the clamp relative to one another orthogonal to a long axis of the rod. At least one of the jaws may define one or more grooves that are complementary to a portion of the external thread. The external thread of the rod may form a crest located between a pair of flanks, and at least one of the jaws of the clamp may be configured to preferentially engage at least one of the flanks relative to the crest when the clamp is locked to the rod.

The apparatus and methods of the present disclosure may offer various advantages over the prior art. Exemplary advantages may include quick and easy assembly and disassembly, full adjustability without the need for tools, and/or fewer user interfaces at which the apparatus is adjusted. Additional and/or alternative exemplary advantages may include rapid translational and/or rotational movement of a nut(s) along the rod, the ability to mount a third assembly (an outrigger) between the first and second assemblies while the first and second assemblies remain coupled to the rod, and/or fewer removable parts. The first and second assemblies each may have no removable parts and thus may be configured such that they cannot be disassembled inadvertently by the user.

Further aspects of the present disclosure are described in the following sections: (I) system overview, (II) rod, (III) stationary base, (IV) slidable base and nut, (V) coupling portion, (VI) outrigger, (VII) methods of distracting/compressing bone, (VIII) system configurations and components, and (IX) selected embodiments.

I. System Overview

This section provides an overview of an exemplary system 40 including a distraction/compression apparatus 50 to hold at least two pins 52a, 52b extending into one or more bones 54, 55; see FIG. 1.

Apparatus 50 may be provided in an assembled form or as a plurality of separate components for assembly by a user. The apparatus may comprise a threaded rod 56 and a pair of pin-holding assemblies 58, 60 (interchangeably called pin holders). Each pin-holding assembly 58, 60 connects a respective pin 52a, 52b to the rod. The axial distance along rod 56 between assemblies 58, 60 (and the distance between pins 52a, 52b) is adjustable by axial movement of the assemblies relative to one another, at least one of which is slidable along the rod parallel to a long axis 62 thereof. For example, in the depicted embodiment, fixed pin-holding assembly 58 has a stationary base 64 that is mounted to rod 56 at a fixed axial position on the rod, and movable pin-holding assembly 60 has a slidable base 66 that is coupled slidably to the rod. Further aspects of rod 56, stationary base 64, and slidable base 66 are described elsewhere herein, such as in Sections II-IV.

In some embodiments, travel of slidable base 66 may be guided axially on rod 56 by interaction between at least one anti-rotation feature 68 of the base and at least one anti-rotation feature 70 defined by rod 56. The anti-rotation features of rod 56 and slidable base 66 are configured to mutually obstruct rotation of the base about the rod while permitting translational motion of the base along the rod. In the depicted embodiment, anti-rotation feature 70 of rod 56 is a slot, and anti-rotation feature 68 is a projecting member located at least partially in the slot. In other embodiments, anti-rotation features 68, 70 may produce any suitable, corresponding deviations from circular symmetry (feature(s) 68) and uniform thread depth (feature(s) 70). For example, each anti-rotation feature 68 may be a flat facing an anti-rotation feature 70 that is also a flat. As another example, anti-rotation feature 68 may include a recess, and anti-rotation feature 70 may include at least one projecting member configured to be located at least partially in the recess.

Axial movement of pin-holding assembly 60 parallel to long axis 62 may be limited and driven by one or more nuts 72a, 72b configured to be in threaded engagement with rod 56. The nuts may (or may not) be substantially identical to one another. In the depicted embodiment, outside nut 72a (not located between assemblies 58, 60) can be rotated about the rod and against slidable base 66 of movable assembly 60, to drive movable assembly 60 toward fixed assembly 58 and apply compressive force to bone. Inside nut 72b (located between assemblies 58, 60) can be rotated about the rod and against slidable base 66 of movable assembly 60, to drive the movable assembly away from fixed assembly 58 and apply distractive force to bone. In some embodiments, each nut may have parts that move relative to one another to change the nut between a slidable configuration and a rotatable configuration. In the slidable configuration, the nut can slide axially along long axis 62 without engaging an external thread 74 of the rod (for gross adjustment of the nut's axial position). In the rotatable configuration, the nut can engage external thread 74 and move by threaded advancement as the nut is rotated (for fine adjustment of the nut's axial position). Further aspects of nuts 72a, 72b are described elsewhere herein, such as in Section IV.

Each pin-holding assembly 58, 60 may have a coupling portion 76 that engages a base (64 or 66) and a corresponding pin (52a or 52b), to connect the base to the pin. Coupling portion 76 may be firmly attachable to both the base and the pin. For example, in the depicted embodiment, the coupling portion has a clamp 78 for attachment to the base, a tube 80 to receive a section of the pin, and a set screw 82 to lock the pin to the tube. A user interface, such as a single graspable member 84, may be manipulated by a user (e.g., rotated) to change the coupling portion between adjustable and fixed configurations. In the adjustable configuration, the orientation of tube 80 (and particularly a long axis 86 thereof) may be adjustable, with respect to the corresponding base (64 or 66) in at least one plane and/or in a pair of non-parallel planes (such as a pair of orthogonal planes). For example, the orientation may be adjustable in a first plane that is orthogonal to long axis 62 of rod 56 and in a second plane that is parallel to long axis 62. In the fixed configuration, the orientation of long axis 86 in both planes may be fixed with respect to the corresponding base. Further aspects of coupling portion 76 are described elsewhere herein, such as in Section V.

Apparatus 50 optionally may comprise a third assembly, an outrigger 88, that is mountable to rod 56. The outrigger may engage external thread 74 of the rod using a clamp 90. Accordingly, the outrigger may be mounted to rod 56 between bases 64, 66, or between one end of the rod and both bases. A section of rod 56 may be positioned between the jaws of clamp 90 by moving the clamp and the rod relative to one another orthogonal to the long axis of the rod, before the jaws are tightened against the rod. In other words, clamp 90 may be placed onto the rod from a position lateral to the rod, without access to either end of the rod. This side-loading ability may permit the outrigger to be mounted to the rod between bases 64 and 66, and removed from the rod, while both bases 64 and 66 remain coupled to the rod (e.g., fixed in position on the rod).

The outrigger may include an elongated portion 92 coupled to clamp 90. Elongated portion 92 may have a proximal region forming a user interface, such as a graspable member 94, and a distal region including an arm 96. Graspable member 94 may be manipulated (e.g., rotated) to open and close clamp 90 and to fix the orientation of arm 96 with respect to the clamp (and rod 56). In some embodiments, the orientation of a long axis defined by arm 96 may be adjustable in a plane parallel to long axis 62 of rod 56. A distal clamp 98 may mount a third pin 52c or a tool to arm 96. The third pin may hold a bone fragment in place while a fixation device, such as a plate, is being attached to the bone fragment. Exemplary tools that may be mounted to the arm include a bone clamp, a tissue spreader, a depth gauge, or a joint alignment guide, among others. An exemplary guide that may be suitable for joint alignment of a subject's leg is described in U.S. patent application Ser. No. 15/654,641, filed Jul. 19, 2017, which is incorporated herein by reference. Further aspects of outrigger 88 are described elsewhere herein, such as in Section VI.

Pins 52a, 52b, and 52c (if present) may be placed in any suitable bone or bones, and with any suitable portion of each pin protruding from the bone. In the depicted embodiment, pin 52a is installed in tibia 54, pin 52b in femur 55 at a position anatomically proximal to a fracture 100 of the femur, and pin 52c in the femur at a position between fracture 100 and the knee. Other bones, and discontinuities therein, that may be suitable for use with apparatus 50 are described below in Section VII.

Each pin 52a-52c may have any suitable structure. The pin may have an elongated shaft, which may or may not be cylindrical. At least a section, such as at least a leading section, of the pin may be externally threaded, or the pin may be non-threaded. A trailing end section of the pin may be configured to be engaged with the collet of a driver, and may, for example, include at least one flat 102. The pin may or may not have a head formed at its trailing end. Exemplary pins that may be suitable include Schanz pins/screws, Steinmann pins, or the like, among others.

II. Rod

This section describes further aspects of exemplary rod 56 of apparatus 50 (see FIG. 1), and an exemplary rod extension 104 for attachment to an end of the rod to increase the rod's effective length; see FIGS. 2, 2A, 3, and 4.

FIG. 2 shows rod 56 and rod extension 104 arranged coaxially on long axis 62 for mating to form a rod assembly 106 of greater length. Rod 56 may have a threaded portion 108 including at least one external thread 74, and a nonthreaded portion 110 continuing axially from the threaded portion and forming one of the opposite ends 112, 114 of the rod. The rod may have a single external thread following only one helical path, or two or more external threads following two or more helical paths, generally of the same pitch, that are offset from one another axially by less than the pitch, among others.

Nonthreaded portion 110 may define various surface features 116 for engagement by stationary base 64 (see FIG. 1 and Section III) or rod extension 104, when mounted to the rod. These surface features may be configured to restrict axial motion of the base or rod extension along long axis 62 of the rod and/or to restrict rotational motion of the base or rod extension about the long axis. For example, nonthreaded portion 110 may define a neck region 118 of reduced diameter to restrict axial motion of the base or rod extension. The neck region may be described as a circumferential recess extending partially or completely around long axis 62. The nonthreaded portion also or alternatively may define at least one axial depression 120. Each depression 120 may be elongated parallel to long axis 62, and may extend substantially to the terminus of end 114. In the depicted embodiment, rod 56 defines a pair axial depressions 120 offset by 180 degrees about long axis 62, but any number of depressions and/or any amount of angular offset may be suitable.

Rod extension 104 may have an elongated shaft 122. The shaft may be hollow, to permit at least part of the length of nonthreaded portion 110 of rod 56 to be received inside the shaft (see FIGS. 2A and 3). In the depicted embodiment, shaft 122 defines a channel 124 that extends completely through the shaft along the long axis thereof. Shaft 122 may have an nonthreaded portion 110a that matches nonthreaded portion 110 of the rod, such as defining surface features 116a (e.g., a neck region 118a and axial depressions 120a) that are similar to the rod's surface features 116. This design allows base 64 (see FIG. 1) or one or more additional copies of rod extension 104 to be mounted to the end of shaft 122. The shaft also may include a mating protrusion 126 configured to be received in one of axial depressions 120 when the rod and the rod extension are axially mated with one another, to restrict rotation about the long axis of the rod. Protrusion 126 may be formed integrally or by a discrete component, such as a short peg, that is attached to the body of the shaft and protrudes inward.

Rod extension 104 may include a retaining member 128 that moves into and out of neck region 118 to respectively restrict and permit axial removal of the rod extension (see FIG. 3). For example, in the depicted embodiment, the rod extension has a pair of balls 130 each located partially in a respective bore 132 defined by shaft 122. Each ball 130 is movable radially with respect to shaft 122, between a retaining position in which the ball is partially positioned in the depression of neck region 118 (as in FIG. 3), and a non-retaining position in which the ball does not block removal of the rod extension from the rod.

The position of each ball 130 may be controlled by a collar 134 connected coaxially to rod extension 104. Collar 134 may have an axial position biased by a spring 136. A clip 138 may set a limit for travel of collar 134, and may hold the collar on shaft 122. The collar may include a blocking structure 140 that prevents outward travel of ball 130 until blocking structure 140 is moved. A user may slide collar 134 axially on shaft 122 in a direction away from clip 138 to compress spring 136, which allows ball 130 to move radially outward, and rod extension 104 to be removed axially from rod 56.

FIGS. 2, 2A, and 4 show an anti-rotation feature 70 defined by rod 56 and intersecting external thread 74. Each anti-rotation feature 70 may be a slot (as depicted), a flat, or other structure formed in external thread 74. An anti-rotation feature 70 may be elongated along rod 56, such as parallel to long axis 62, and may be linear. The anti-rotation feature may have an open end (see FIG. 4), while the opposite end thereof may (or may not) be closed. Anti-rotation feature 70 may eliminate a portion (e.g., a short section 141) of thread 74 from each of a plurality of successive turns thereof, such as at least a majority of the turns of the thread. Short section 141 may or may not be eliminated down to a root 142 of thread 74. Accordingly, a bottom surface region 143 of anti-rotation feature 70 may or may not be closer to long axis 62 than root 142. Each anti-rotation feature 70 may extend for a majority of the length of rod 56 and/or a majority of the length of threaded portion 108. The anti-rotation feature may be substantially uniform in depth and width along its length. Anti-rotation feature 70 and a depression 120 defined by nonthreaded portion 110 may have substantially the same circumferential position as one another around the rod, such as located on the same side of rod 56 and bisected by the same plane containing long axis 62 (see FIGS. 2 and 2A).

III. Stationary Base

This section describes further exemplary aspects of stationary base 64 of fixed pin-holding assembly 58 in apparatus 50 of FIG. 1, and of a mounting interface for locking base 64 to rod 56 at each position (and/or orientation) of a predefined series of rotational positions (and/or radial orientations) about the long axis of the rod; see FIGS. 5-9.

FIG. 5 shows base 64 of the fixed pin-holding assembly 58 mounted to nonthreaded portion 110 of rod 56 (also see FIGS. 1 and 2). In some embodiments, base 64 (and/or base 66) or the corresponding pin-holding assembly 58 (and/or assembly 60) may be called a tower or a tower assembly. Base 64 may form a frame including a sleeve 144 defining an axial opening, such as an axial through-opening, to receive at least a section or all of nonthreaded portion 110. The base may have one or more legs 146 attached (such as firmly attached) to sleeve 144. The proximal end of each leg 146 may be adjacent and attached to sleeve 144. The distal ends of legs 146 may be attached (such as firmly attached) to one another with a bridge 147 located opposite sleeve 144 to create a closed loop frame, as shown here. Sleeve 144 and bridge 147 may be offset from one another by legs 146 in a direction orthogonal to long axis 62 of rod 56, after base 64 is mounted to rod 56. The sleeve and the bridge may define respective axes that are parallel to and spaced from one another. In some embodiments, the diameter of each leg 146 may be the same as the diameter of bridge 147, to facilitate attaching the same size of clamp to either leg or the bridge.

Rod 56 and base 64 may define respective mating structures 148 and 149 (or 149a) that are at least partially complementary to another (see FIGS. 6-8). The mating structures may be mated with one another by axial motion of rod 56 and base 64 relative to one another, to restrict rotation relative to one another about long axis 62 of the rod. For example, rod 56 may have one or more recesses 150 that are complementary to one or more corresponding projections 152 (or 152a) of base 64, or vice versa, or a combination thereof, among others. The mating structures may be configured to mate with one another in only one rotational position of the base or in each of a plurality of different, alternative rotational positions (and/or radial orientations) of the base about rod 56, to set the rotational position/radial orientation of the base. The positions/orientations may be offset from one another by any suitable offset angle, such as 180, 120, 90, 60, or 45 degrees, among others. Accordingly, the position/orientation of base 64 may be rotationally adjustable by predefined increments. In the depicted embodiment, mating structure 148 of rod 56 defines a circumferential series of axial recesses 150 (see FIG. 6), and mating structure 149 of base 64 has a pair of projections 152 that fit alternatively into each opposite pair of recesses 150 (see FIGS. 7 and 8). Projections 152 (and 152a) may be formed integrally with sleeve 144, or may be formed separately therefrom, as in the depicted embodiment (see FIG. 8).

Base 64 may be configured to be mounted to rod 56 entering either end of sleeve 144. The base may have respective projections 152, 152a positioned at each end of sleeve 144 for fitting together with recesses 150 of rod 56 (see FIG. 8). Accordingly, the base may be symmetrical.

Figure 9:
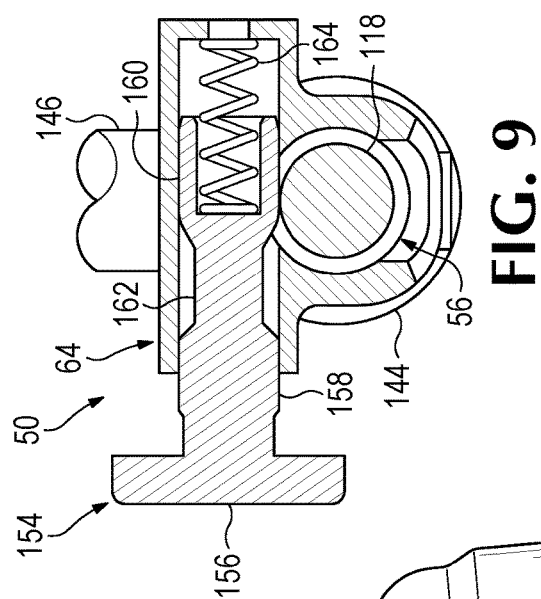
FIG. 9 is a fragmentary, sectional view of the rod and base of FIG. 5, taken generally along line 9-9 of FIG. 5.

Axial removal of base 64 from rod 56 may be restricted by a locking member 154 that is movably coupled to the base (see FIGS. 5, 7, 8, and 9). The locking member may interact with neck region 118 of rod 56, or neck region 118a of rod extension 104 (see FIG. 2), to obstruct separating translational motion of base 64 parallel to long axis 62 of rod 56. Locking member 154 may have a head 156 and a shaft 158, and the shaft may have a wider region 160 and a narrower region 162. A spring 164 may bias the position of locking member 154 to a securing configuration, as shown in FIGS. 8 and 9. In this configuration, wider region 160 is partially located in the depression formed by neck region 118, such that contact between wider region 160 of shaft 158 and the wall of neck region 118 prevents removal of the base from the rod. To unlock base 64 from rod 56, a user may manipulate locking member 154 to move narrower region 162 into alignment with neck region 118. For example, in the depicted embodiment, a user may apply pressure to head 156, which forms a button, to compress spring 164, which places locking member 154 in a releasing configuration. With locking member 154 held in the releasing configuration (i.e., the unlocked configuration of base 64), the user may disengage mating structures 148, 149 from one another axially. Rod 56 and base 64 may be rotated relative to one another about long axis 62 of rod 56. Mating structures 148, 149 may be mated with one another in a different configuration to establish a different rotational position (and/or radial orientation) of the base about the rod. Pressure on locking member 154 may be removed, to allow the locking member to return to its securing configuration, to lock the base to the rod in the different rotational position. Alternatively, the user may unlock base 64 by moving locking member 154 to its releasing configuration, and base 64 may be removed axially from rod 56. Locking member 154 and neck region 118 may be arranged such that the locking member can lock base 64 to rod 56 at the neck region when end 114 of rod 56 is advanced into either end of base 64.

In some embodiments, pin-holding assembly 58 and/or base 64 may be coupled to rod 56 during manufacture of the apparatus. For example, base 64 of assembly 58 may be pre-attached to rod 56, optionally firmly and/or non-removably, before the apparatus is supplied to the user.

IV. Slidable Base and Nut

This section describes further exemplary aspects of slidable base 66 and nut 72b (and/or nut 72a) of apparatus 50 of FIG. 1; see FIGS. 10-12, 12A, and 13-15.

Figure 10:
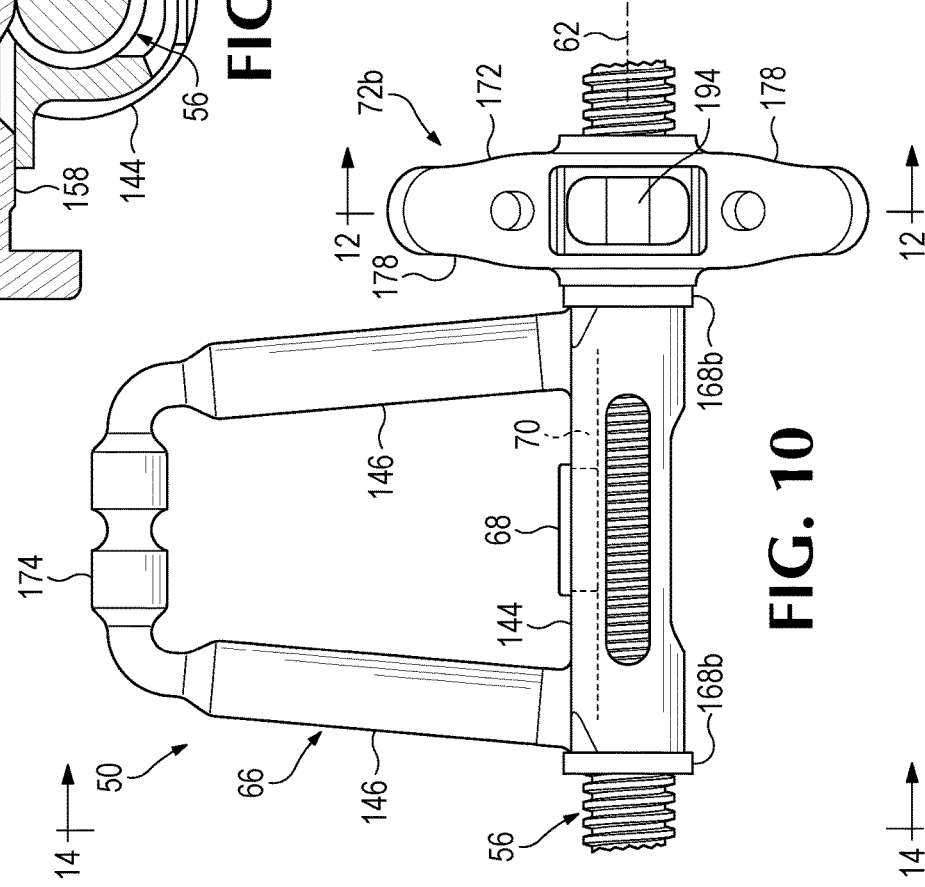
FIG. 10 is another fragmentary, elevation view of selected aspects of the apparatus of FIG. 1, taken around a movable pin-holding assembly and a distraction nut of the apparatus but showing only a base of the assembly slidably disposed on the rod.

FIG. 10 shows base 66 of movable pin-holding assembly 60 slidably coupled to rod 56. Slidable base 66 may have any suitable combination of the features described above for stationary base 64, such as a frame formed by a sleeve 144, one or more legs 146, and/or a bridge 147, among others (compare with FIG. 5). However, slidable base 66 may lack locking member 154. Also, projections 152, 152a for mating with recesses 150 of rod 56 may be replaced with at least one anti-rotation feature 68 for interaction with at least one anti-rotation feature 70 of rod 56 (also see FIGS. 14 and 15). Anti-rotation feature 68 may allow translational movement of base 66 along anti-rotation feature 70, while restricting rotational motion of base 66 relative to rod 56 about long axis 62. Each anti-rotation feature 68 may be formed integrally with sleeve 144 or, as in the depicted embodiment, may be provided by another component that is formed separately and attached to the sleeve. Sleeve 144 may define an axial channel 166 extending between opposite ends of the sleeve, and each anti-rotation feature 68 may project into channel 166, such as projecting radially inward with respect to the channel. Anti-rotation feature 68 may have a width that matches the width of an anti-rotation feature 70 and/or may be elongated parallel to the long axis of sleeve 144 (and anti-rotation feature 70), to minimize wobble of base 66, while permitting base 66 to slide freely along the rod. In some embodiments, sleeve 144 may include at least a pair of anti-rotation features 68 that are spaced from one another about or along the long axis of the sleeve. For example, the sleeve 144 may form a pair of projecting members received in a pair of slots of rod 56, the sleeve may form a pair of flats that are rotationally offset from one another and that interact with corresponding flats defined by the rod (e.g., in the external thread thereof).

Base 66 may have a symmetrical configuration, as shown, that permits the base to be slidably coupled to rod 56 at anti-rotation feature 70 when end 112 of the rod enters sleeve 144 from either end thereof (also see FIG. 2). Anti-rotation feature 70 may have an open end 167 that allows anti-rotation feature 68 to access feature 70 parallel to the feature's long axis, as sleeve 144 is being placed onto rod 56. Open end 167 may be located opposite stationary base 64 after base 64 has been mounted to an end of the rod. Base 66 and/or pin-holding assembly 60 may be slidably pre-coupled to rod 56 during manufacture of the apparatus, or coupled to the rod by the user (e.g., in the operating room).

Apparatus 50 may have features, which may be color-coded, that help a user to quickly determine which base 64 or 66 should be assembled with each end of rod 56 (see FIGS. 2, 5, 8, and 14). For example, rod 56 may have respective rings 168a, 170a of different color at opposite ends 112, 114. Base 64 may have a pair of rings 170b at opposite ends of sleeve 144 that match the color of ring 170a. Base 66 may have a pair of rings 168b at opposite ends of sleeve 144 that match the color of ring 168a (since the rod may be received from either end).

One or both nuts 72a and 72b may be configured to be adjusted between engagement with external thread 74, and disengagement from the thread, at any position along the threaded portion of rod 56 (see FIGS. 10, 11, 12A, 12B, and 13). The nut may have a body 172 and a securing member 174 that are movably connected to one another. Body 172 may define an aperture 176, such as a circular aperture, through which rod 56 can extend. Aperture 176 may be sized to permit the rod to slide freely when thread 74 is not engaged by securing member 174. One or a plurality of wings 178 may project away, such as radially, from the central portion of body 172. In some embodiments, the nut has two wings opposite one another, three wings (e.g., offset from one another by 120 degrees), or four wings (e.g., offset from one another by 90 degrees), among others. The wings facilitate grasping and manipulating the nut by hand.

Figure 12:
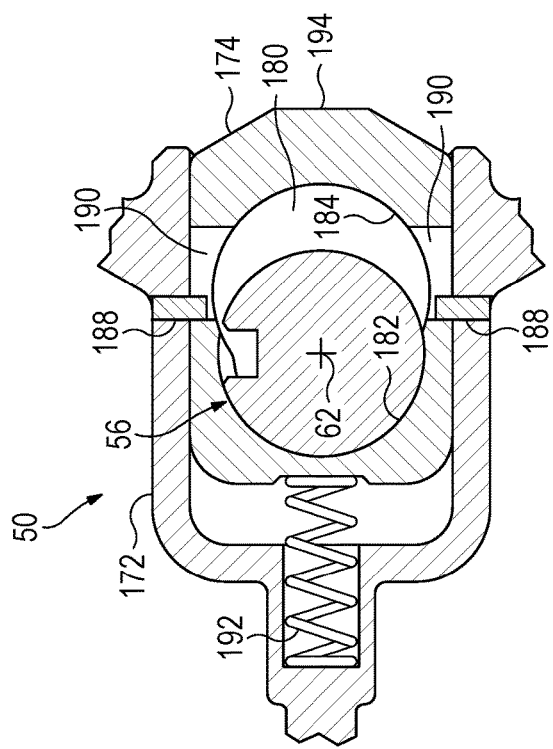
FIG. 12 is a sectional view of the rod, base, and nut of FIG. 10, taken generally along line 12-12 of FIG. 10, with a securing member of the nut engaged with an external thread of the rod.

Securing member 174 may define a through-opening 180 having a grooved region 182 and a slidable region 184 (see FIGS. 12, 12A, and 13). Grooved region 182 may be complementary to a portion of thread 74 and configured to be disposed in engagement with thread 74 from a position lateral to the rod. The grooved region may have at least one or a plurality of grooves 186 that are complementary to one or more correspondingly-sized lengths of external thread 74. Grooved region 182 may define major and minor diameters matching the major and minor diameters of thread 74. In contrast, slidable region 184 is configured to avoid engagement with thread 74. Slidable region 184 may define a minimum diameter that is greater than the major diameter of thread 74, to enable the nut to travel freely over thread 74 without engaging the thread.

Securing member 174 may be movable with respect to body 172 in a direction transverse (e.g., orthogonal) to long axis 62 of rod 56. A pair of pegs 188 fixed to body 172 may slide in openings 190 defined by securing member 174. The openings may be elongated orthogonal to long axis 62. A spring 192 of the nut may bias securing member 174 toward a deployed configuration shown in FIGS. 11 and 12.

Figure 11:
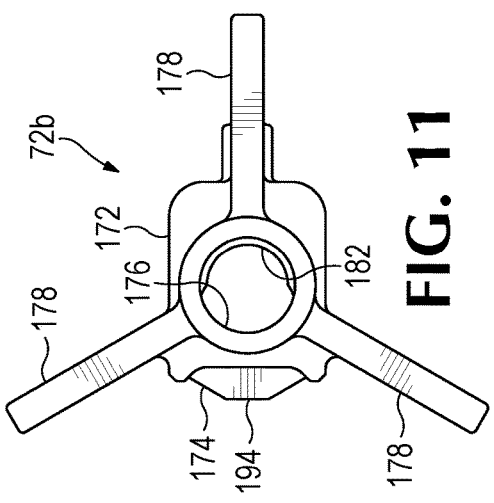
FIG. 11 is an axial view of the distraction nut of FIG. 10 taken in isolation.

In the deployed configuration, grooved region 182 may be located closer than the perimeter of body aperture 176 to a central through-axis defined by the aperture (see FIG. 11). Rod 56 may be engaged on one side by grooved region 182 and contacted on an opposite side by a wall of aperture 176. Engagement between grooved region 182 and external thread 74 prevents translational motion of rod 56 parallel to long axis 62 (see FIG. 12). However, the nut may be rotated to adjust its position along the threaded portion of the rod by threaded advancement on thread 74.

A user may apply pressure to a button 194 formed by securing member 174 to urge the securing member from the deployed configuration shown in FIG. 12 to a retracted configuration shown in FIG. 12A (also see FIG. 11). In the retracted configuration, slidable region 184 of securing member 174 may be aligned with aperture 176, while grooved region 182 is separated from thread 74 and does not obstruct motion of rod 56. Accordingly, the nut can slide freely on rod 56 such that translational motion of the nut along the rod parallel to long axis 62 is permitted, for placement of the nut onto the rod and/or gross adjustment of the position of the nut along the rod.

In some embodiments, whether or not the nut has moving parts as described above, the nut and the rod may be configured to have a low-friction, threaded coupling with one another when the nut is not under axial load (e.g., when the nut is not exerting pressure on the second assembly). This low-friction coupling may allow the nut to spin substantially freely about the rod, to provide rapid, threaded travel of the nut along the external thread with minimal user effort. For example, the nut may have one or more wings (such as one or more radial wings) that can be flicked with the user's hand (e.g., a finger(s) thereof) to drive rotation of the nut. Optionally, the nut and the rod may be configured such that a single flick of one of the wings with a user's finger can cause the nut to spin at least about 2, 4, 6, 8, or 10 revolutions about the rod, and/or travel at least about 1, 2, or 4 centimeters along the rod, among others. In some embodiments, each wing may be elongated transverse to the long axis of the rod, such as elongated radially. In some embodiments, each wing may have an outer end configured to be located at a distance from the long axis of rod that is substantially greater than the radius of the rod measured at the external thread, to enable application of more torque to the nut with the user's hand. The distance may, for example, be at least about 3, 4, or 5 times the radius of the rod.

V. Coupling Portion

This section describes further aspects of exemplary coupling portion 76 for either of the pin-holding assemblies 58, 60 of apparatus 50 of FIG. 1; see FIGS. 16-18, 19A, 19B, 20A, and 20B.

Coupling portion 76 may be configured to connect pin 52a or 52b to base 64 or 66 of the pin-holding assembly. The coupling portion may permit changing the orientation of the pin and/or the orientation of pin-receiving axis 86 defined by a pin-receiving structure, such as tube 80 of the coupling portion. (The orientation of pin-receiving axis 86 may be adjusted before and/or after the pin is arranged substantially coaxially with axis 86.) The orientation may be adjusted with respect to the corresponding base 64 or 66 (and with respect to rod 56) in each of a pair of planes that are transverse (e.g., orthogonal) to one another and then the orientation may be fixed.

Figure 16:
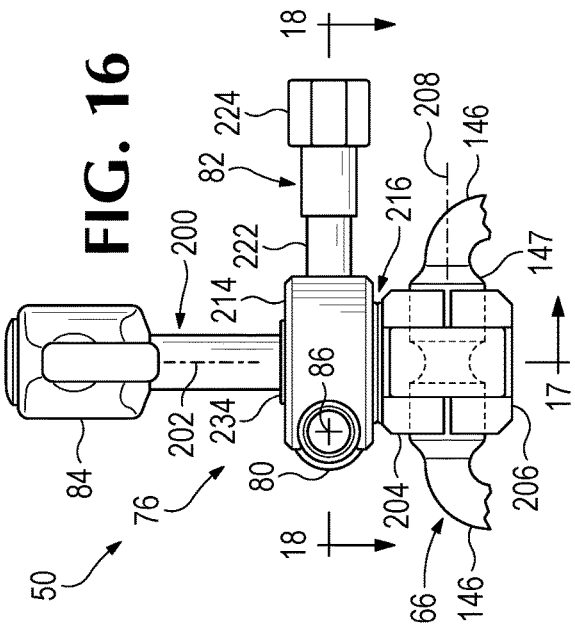
FIG. 16 is a fragmentary view of either pin-holding assembly of the apparatus of FIG. 1, taken around a coupling portion of the assembly.
Figure 18:
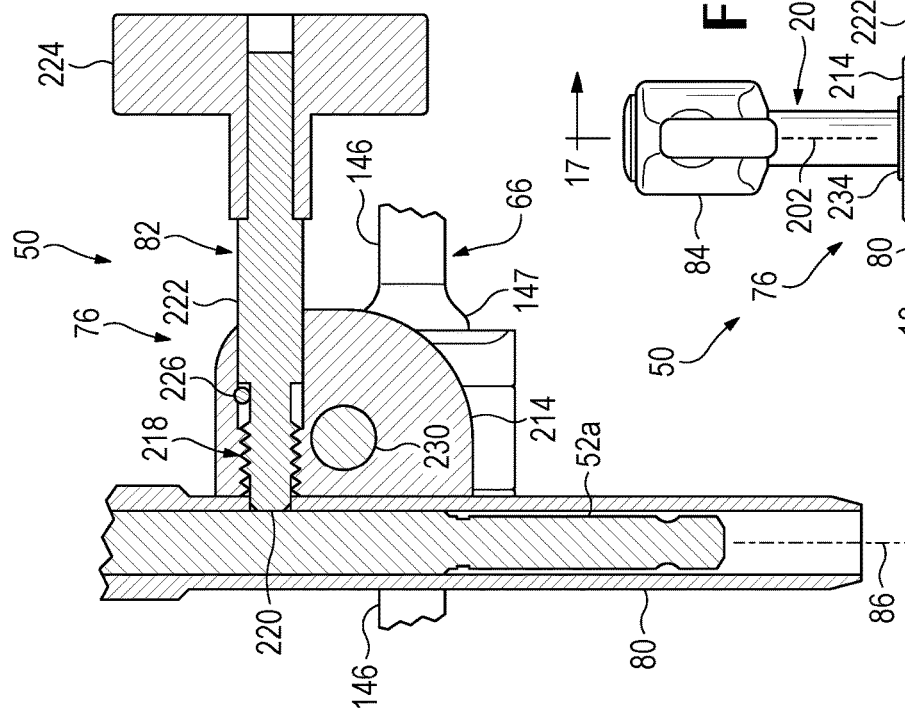
FIG. 18 is a fragmentary, sectional view of the pin-holding assembly of FIG. 16, taken generally along line 18-18 of FIG. 16 in the presence of a pin that is locked to the assembly.
Figure 17:
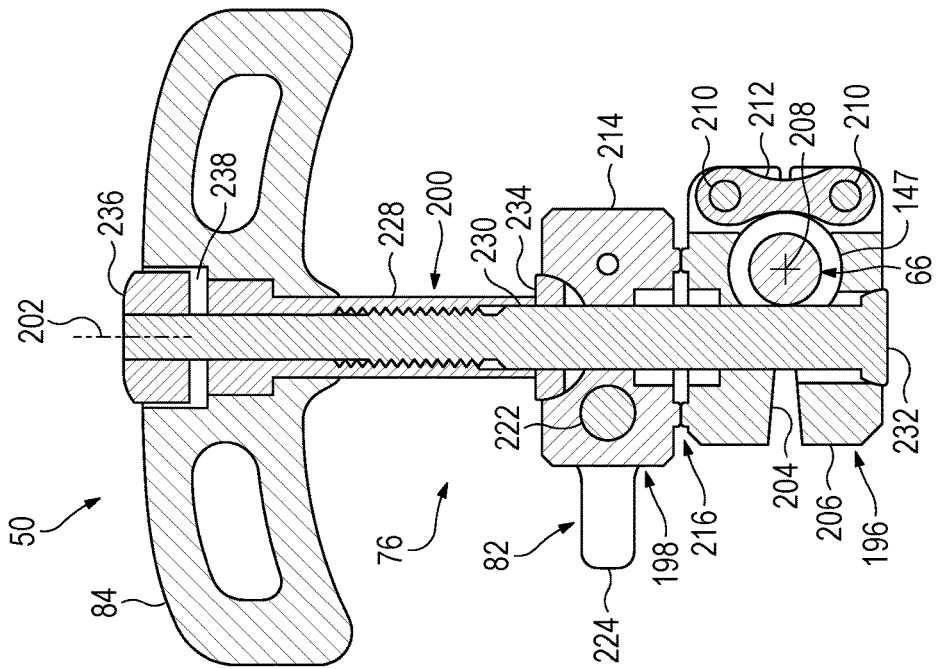
FIG. 17 is a sectional view of the coupling portion of FIG. 16, taken generally along line 17-17 of FIG. 16.
Figure 19A:
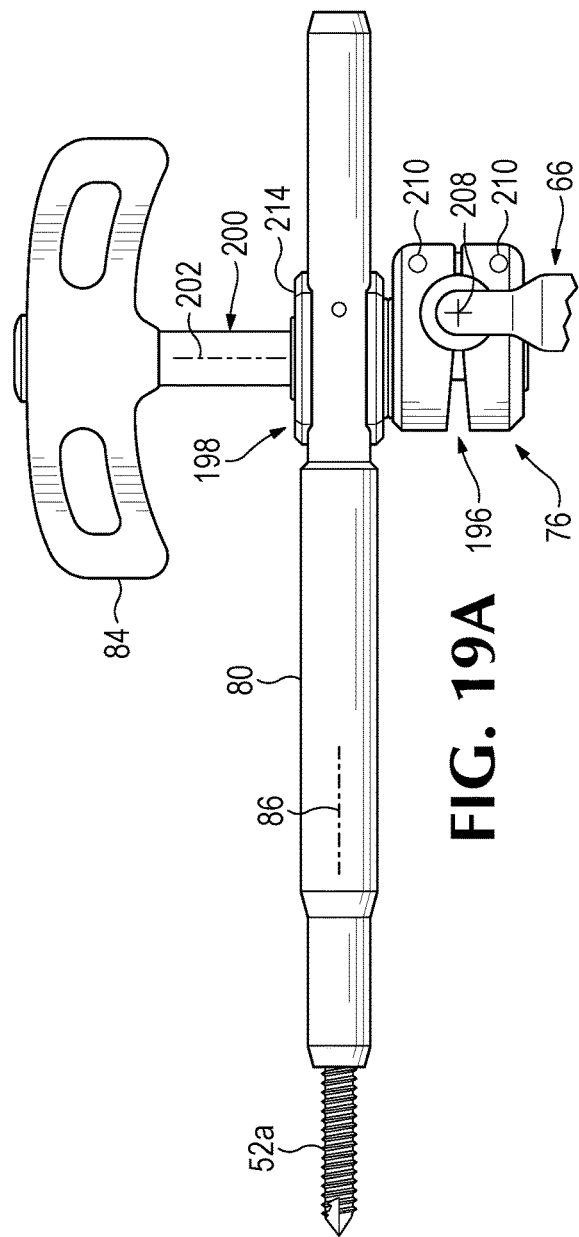
FIGS. 19A and 19B are fragmentary, end views of the pin-holding assembly of FIG. 16, taken with a tube of the assembly in two different orientations, to illustrate angular adjustability of the tube in a plane transverse (e.g., orthogonal) to a long axis defined by the rod.
Figure 19B:
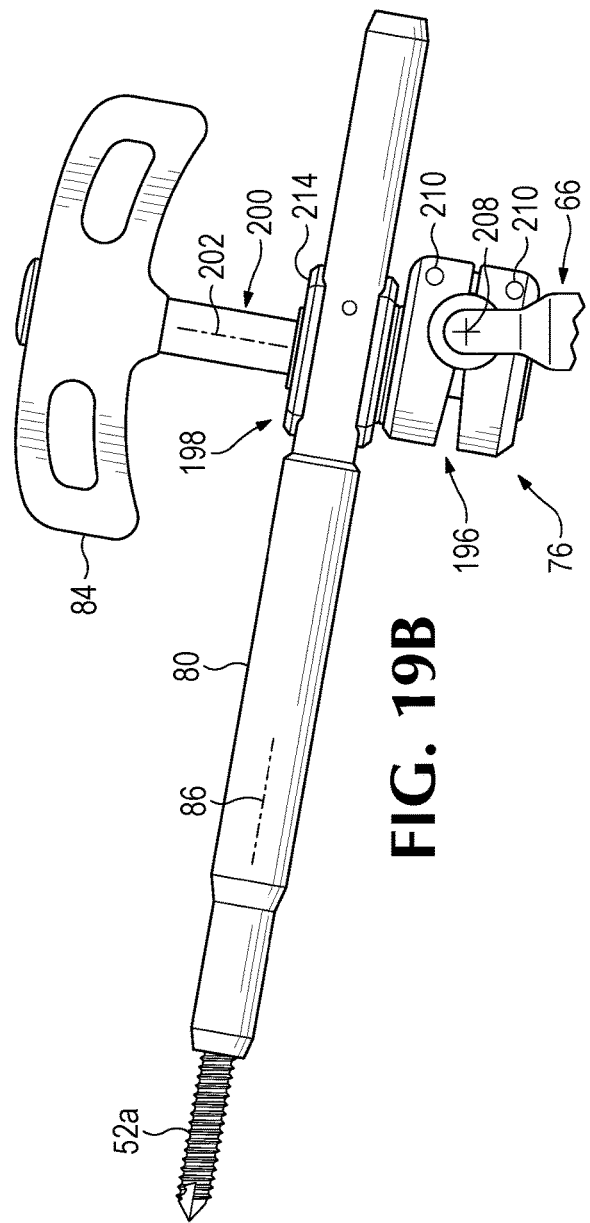

Coupling portion 76 may comprise a clamp 196, a pin support 198, and a fastening assembly 200 defining a fastening axis 202 (see FIGS. 16-18). Clamp 196 may provide attachment to base 66 (or 64). Pin support 198 may define pin-receiving axis 86 and may be configured to lock a pin to the pin support. Fastening assembly 200 may be manipulated to change coupling portion 76 between an adjustable configuration and a fixed configuration for the orientation of pin 52a (or 52b) and/or pin-receiving axis 86 in each plane of a pair of non-parallel planes.

Clamp 196 may be configured to grip a section of either base 64, 66, such as a section of a leg and/or a bridge of the base, among others. The orientation of the moment arms within the clamp may create a very high compressive force on the section of the base, to resistant slippage of the clamp.

Clamp 196 may have a pair of jaws 204, 206 to cooperatively grip the section of base 66 (see FIGS. 16, 17, 19A, and 19B). For example, as shown, the clamp may grip a section of bridge 147 defining a bridge axis 208 that extends through clamp 196. Bridge axis 208 may be parallel to long axis 62 of rod 56 (also see FIG. 1). The orientation of coupling portion 76 (and thus pin-receiving axis 86) may be adjusted as a unit by rotation of the coupling portion about bridge axis 208 in a plane orthogonal to long axis 62 of rod 56 (compare FIGS. 19A and 19B).

Jaws 204, 206 may be pivotably connected to one another for rotation relative to one another about one or more axes parallel to a through-axis of the clamp (and parallel to bridge axis 208) (see FIG. 17). In the depicted embodiment, a pivotable connection defining two parallel, spaced pivot axes is provided by a pair of pivot pegs 210 and a linking member 212 extending between the pegs.

Pin support 198 may comprise a support body 214, a tube 80 firmly attached to the support body, and a set screw 82 in threaded engagement with the support body (see FIGS. 16-18). The orientation of pin support 198 (and thus pin-receiving axis 86) may be adjusted by rotating the pin support as a unit, with respect to clamp 196, about fastening axis 202 in a plane orthogonal to the fastening axis (compare FIGS. 20A and 20B). Pin support 198 may form an interface 216 with clamp 196 at which movement can occur only in an adjustable configuration of coupling portion 76.

Figure 20A:
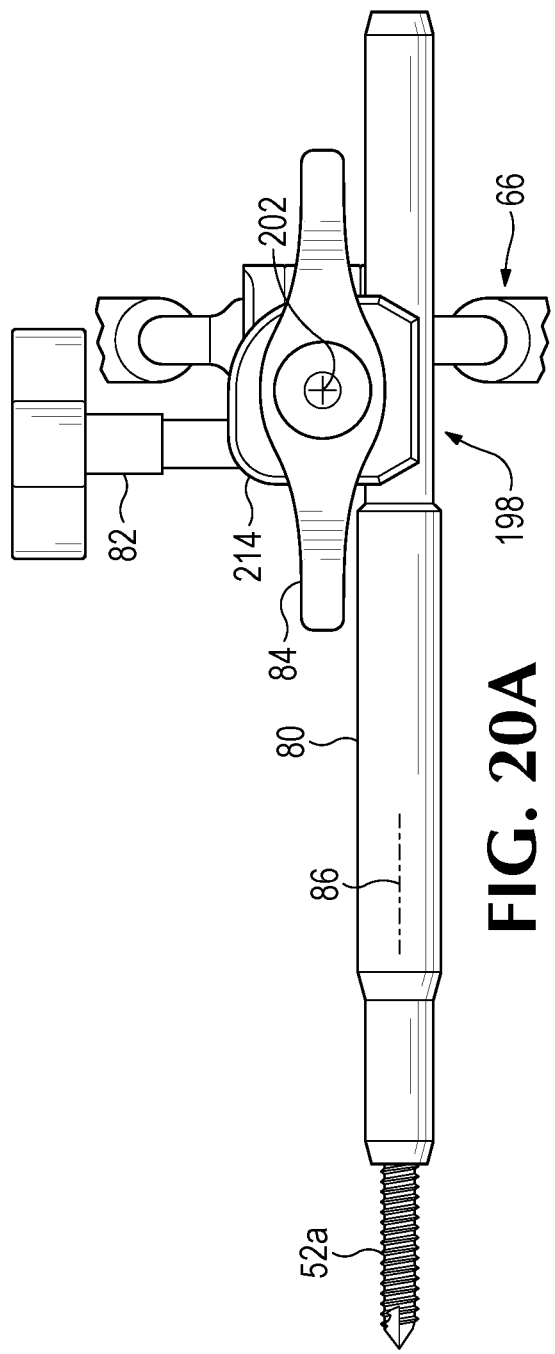
FIGS. 20A and 20B are fragmentary, top views of the pin-holding assembly of FIG. 16, taken with a tube of the assembly in two different orientations, to illustrate additional angular adjustability of the tube in a different plane than in FIGS. 19A and 19B, such as a plane parallel to a long axis defined by the rod.
Figure 20B:
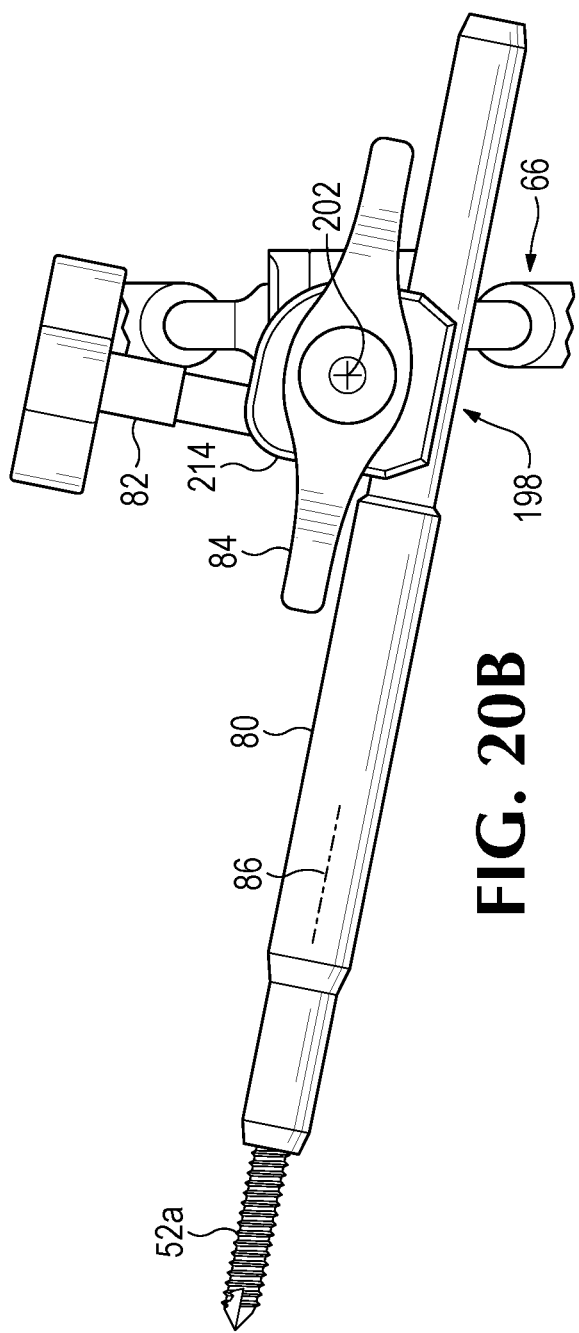

Set screw 82 may not be centered along tube 80 (see FIG. 20A). This arrangement may permit use with pins of different standard lengths. Either a longer pin (e.g., a long Schanz pin as shown) or a shorter pin (e.g., a short Schanz pin) can be locked to tube 80 with set screw 82. For use with a shorter pin, pin support 198 can be rotated 180 degrees about fastening axis 202, and the pin can extend out of the opposite end of tube 80, relative to the configuration of FIG. 20A.

FIG. 18 shows pin 52a locked to tube 80 by set screw 82. The set screw is arranged in threaded engagement with support body 214, indicated with an arrow at 218. A distal end 220 of a shaft 222 of the set screw is in tight contact with pin 52a, to lock the pin to tube 80, which fixes the axial position of the pin along pin-receiving axis 86. A graspable member 224 may be firmly attached to shaft 222, to form an enlarged head. The graspable member can be manipulated (e.g., rotated) by hand to loosen or tighten set screw 82 and/or to assist rotation of pin support 198 relative to clamp 196. A blocking insert 226 may be installed in support body 214 (e.g., during manufacture of pin-holding assembly 58 or 60), after set screw 82 has been installed in support body 214, to prevent inadvertent removal of set screw 82 from support body 214 during use.

Fastening assembly 200 may be configured to apply compression to base clamp 196 and pin support 198, in a direction parallel to fastening axis 202. The fastening assembly may have an internally-threaded component 228 and an externally-threaded component 230 that are in threaded engagement with one another. Rotation of components 228, 230 relative to one another about fastening axis 202 adjusts coupling portion 76 between movable and locked configurations of clamp 196 and pin support 198. The fastening assembly may extend through clamp 196 and pin support 198, and may be configured to apply adjustable pressure on clamp 196 from below and on pin support 198 from above.

One of components 228, 230 may be prevented from rotating about fastening axis 202. For example, in the depicted embodiment, a head 232 of externally-threaded component 230 is seated in a complementary structure formed by lower jaw 206 of clamp 196, to restrict rotation of externally-threaded component 230 with respect to lower jaw 206. The other component 228 or 230 may apply pressure to pin support 198 as the fastening assembly is tightened. For example, in the depicted embodiment, the bottom end of internally-threaded component 228 bears against a collar 234, which transmits pressure to pin support 198. One of components 228, 230 may include a graspable member 84 with which the component can be rotated by hand. In the depicted embodiment, internally-threaded component 228 has a winged handle firmly attached to a shaft.

Fastening assembly 200 may be configured to prevent separation of components 228, 230 from one another during use. A limiting member 236, such as a cap, may be installed during manufacture. The limiting member may be configured to limit the range of axial travel of components 228, 230 relative to one another, to prevent disassembly. In the depicted embodiment, limiting member 236 has been firmly attached to an end of externally-threaded component 230 after components 228, 230 have been threaded together. A gap 238 formed between internally-threaded component 228 and limiting member 236 determines the distance by which internally-threaded component 228 can be retracted before contact between internally-threaded component 228 and limiting member 236 blocks further retraction.

VI. Outrigger

This section describes further aspects of exemplary outrigger 88 of apparatus 50 of FIG. 1; see FIGS. 21-24.

Figure 22:
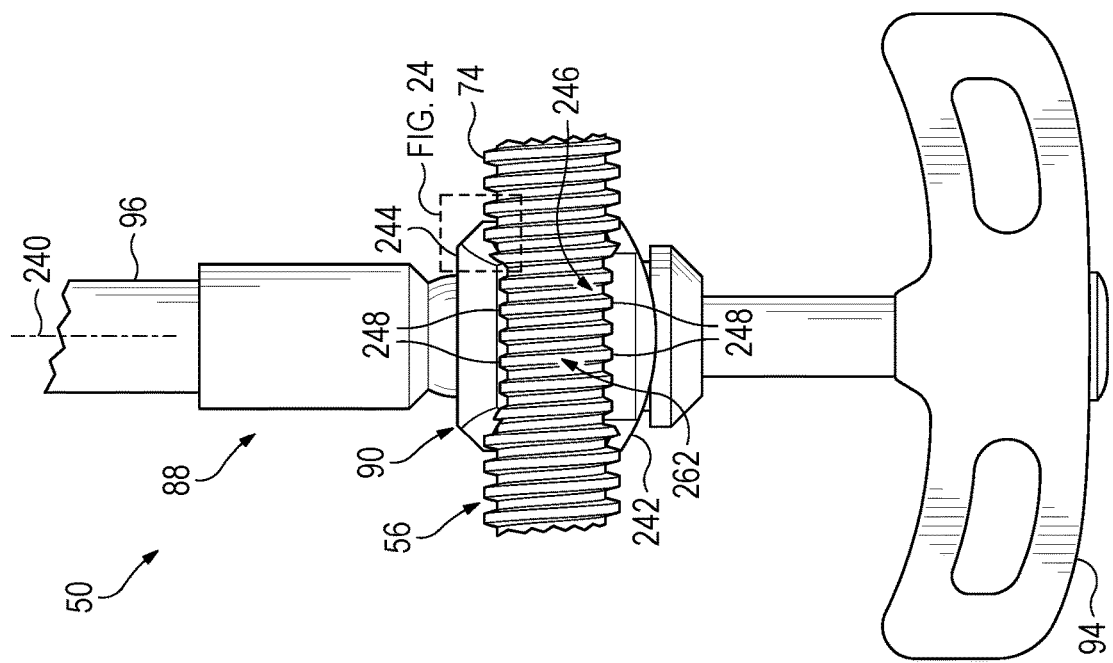
FIG. 22 is another fragmentary view of the apparatus of FIG. 1, taken as in FIG. 21 except showing an opposite side of the outrigger.
Figure 21:
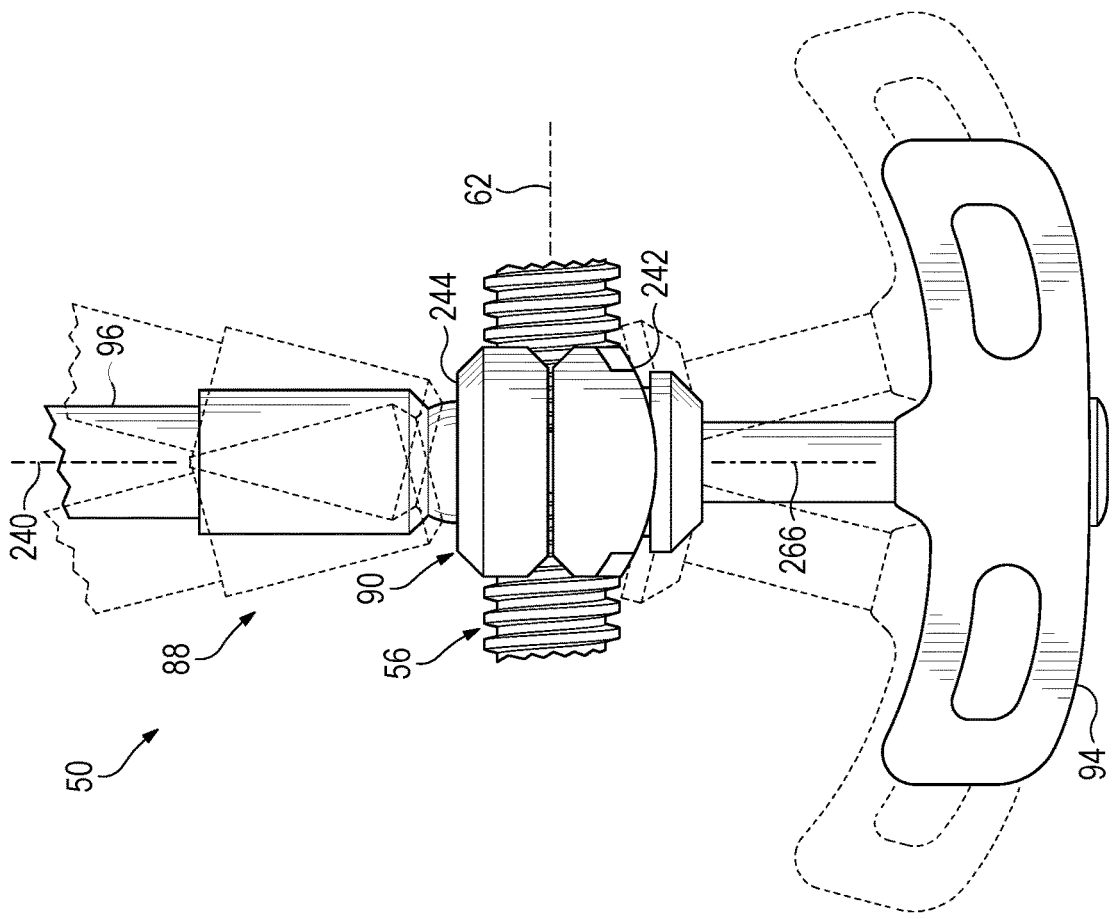
FIG. 21 is a fragmentary view of the apparatus of FIG. 1, taken around a third assembly, namely, an outrigger having a clamp engaged with the external thread of the rod at a position between the first and second pin-holding assemblies of the apparatus, with exemplary adjustability of the orientation of the long axis of the outrigger depicted in dashed outline.
Figure 24:
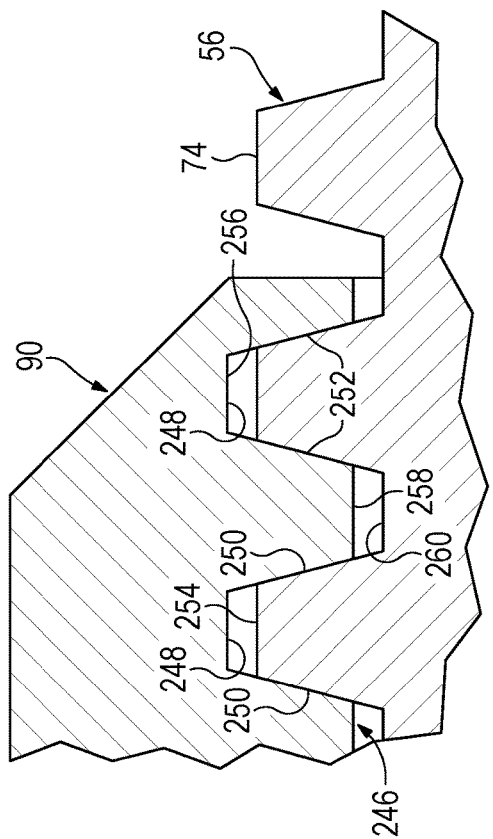
FIG. 24 is fragmentary, sectional view of the outrigger clamp and the rod, taken generally around the region indicated by "FIG. 24" in FIG. 22, and showing an exemplary configuration of engagement between the clamp and an external thread of the rod.

FIGS. 21 and 22 show a proximal portion of outrigger 88 viewed on opposite sides of rod 56. The outrigger defines a long axis 240 and can be firmly attached to rod 56 via clamp 90 at different orientations of long axis 240 (exemplified in dashed outline in FIG. 21). The different orientations may lie in a plane that is parallel to long axis 62 of rod 56.

Clamp 90 may include a proximal jaw 242 and a distal jaw 244. One jaw or both jaws may have a surface region 246 corresponding to a portion of an internal thread, for engagement with external thread 74 of rod 56. Surface region 246 may be complementary to a portion of thread 74 (see FIG. 24), and may define a plurality of grooves 248 to receive corresponding lengths of external thread 74. In the depicted embodiment, clamp 90 may be locked to rod 56 by urging external thread 74 and surface region 246 tightly against one another predominantly at flanks 250 of external thread 74 and flanks 252 of surface region 246, relative to crests and roots thereof. A portion of external thread 74 may be wedged into grooves 248 as clamp 90 is tightened against the rod. However, a crest 254 of external thread 74 may remain apart from a root 256 of surface region 246, and a crest 258 of surface region 246 may remain apart from a root 260 of external thread 74.

Jaws 242, 244 of clamp 90 may form a mouth 262 through which a section of rod 56 may enter clamp 90 (see FIG. 22). Mouth 262 may be opened sufficiently to have a width, measured between jaws 242, 244, that is greater than a diameter of thread 74 of rod 56. With mouth 262 opened to this width, a section of rod 56 may be placed between jaws 242, 244 by motion of rod 56 and clamp 90 relative to one another orthogonal to long axis 62, such that long axis 62 of the rod extends through the clamp between the jaws. The clamp then may be tightened to lock the clamp to the rod.

Figure 23:
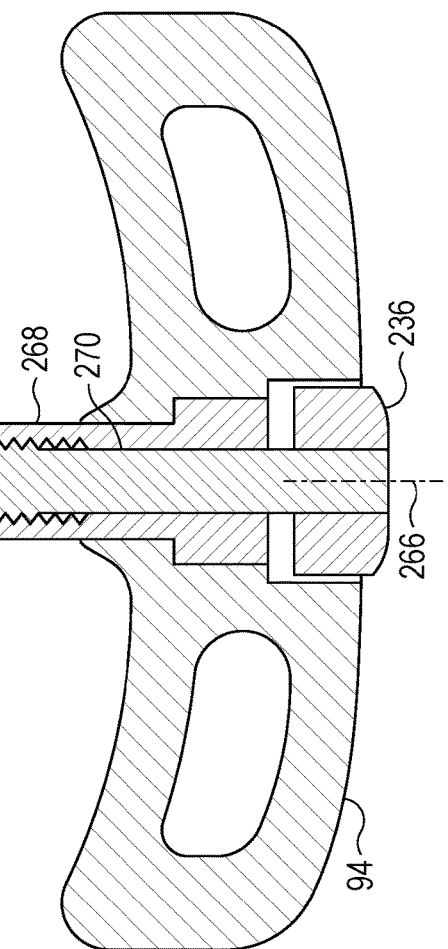
FIG. 23 is a fragmentary, sectional view of the outrigger and rod of FIG. 21, taken through the outrigger in a plane that contains the long axis of the outrigger and is parallel to the long axis of the rod.

FIG. 23 shows a fastening assembly 264 to adjust outrigger 88 between movable and fixed configurations on rod 56. Fastening assembly 264 may be attached (e.g., firmly attached) to arm 96 (also see FIG. 22), and defines a fastening axis 266, which may be arranged parallel and/or coaxial to arm axis 240 (also see FIG. 21). Fastening assembly 264 may include an internally-threaded component 268 and an externally-threaded component 270 in threaded engagement with one another. Rotation of the components relative to another about axis 266 tightens or loosens clamp 90.

Fastening assembly 264 may extend through jaws 242, 244 of clamp 90 opposite mouth 262. More particularly, each jaw may define a respective opening 272, 274 that is elongated parallel to the long axis of the rod. Fastening assembly 264 may pivot at a rotational interface 276, such as a ball joint, formed between a convex, rounded region 278 of fastening assembly 264 and a complementary, concave opening 280 of distal jaw 244. Pivotal motion of the fastening assembly may occur about an axis 282 extending through a center of curvature of interface 276. The pivotal motion may be guided by a collar 284 traveling along an arcuate track 286 formed by a recess of proximal jaw 242 adjacent opening 272. Surfaces of collar 284 and track 286 that slide on each other may define a series of complementary teeth that resist pivotal slippage of fastening assembly 264 about axis 282 when the collar and track are tightened against one another.

Fastening assembly 264 may be structured generally as described above for fastening assembly 200. For example, rotation of graspable member 94 (e.g., a winged handle) may advance or retract internally-threaded component 268 (or externally-threaded component 270) along axis 266. Advancement of the component may urge collar 284 into tight contact with proximal jaw 242 at track 286, which locks clamp 90 to rod 56 and fixes the selected orientation of axis 266 and arm 96. Axial travel of internally- and externally-threaded components 268, 270 relative to one another may be limited by a limiting member 236, as described above for fastening assembly 200.

VII. Methods of Distracting/Compressing Bone

This section describes exemplary methods of distracting and/or compressing bone using the apparatus of the present disclosure. The steps presented in this section may be performed in any suitable order and combination using any of the apparatus components and features disclosed herein.

One or more bones to be distracted and/or compressed may be selected. Any suitable bone or bones of a subject may be selected. An exemplary single bone that may be suitable is a bone of an arm or a leg of a subject (e.g., a femur, tibia, fibula, humerus, ulna, or radius). An exemplary pair of bones that may be suitable articulate with one another at a joint, such as the knee or the elbow. Accordingly, the pair of bones may be a femur and a tibia, a femur and a fibula, a humerus and an ulna, a humerus and a radius, or the like. At least one of the selected bones may have a discontinuity (e.g., a fracture, a cut, a nonunion, or the like) when selected, or may be modified (e.g., cut or broken) to have a discontinuity as the method is performed.

At least a pair of pins each may be driven into the one or more bones of the subject, optionally with threaded engagement between each pin and one of the bones. The pins may be inserted into bone on opposite sides of the discontinuity, such as in different pieces of the same bone, and/or may be placed in different bones. The pins may be inserted into the same side of the bone(s) along axes that are generally parallel, or into different sides of the bone(s) along axes that are offset from one another around the bone(s).

A distraction/compression apparatus may be assembled from components thereof, in any suitable order. Assembly may be performed on a table or other support surface, optionally away from the subject. A first nut may be coupled to a threaded region of a rod, optionally while the first nut is arranged in an axially slidable configuration. A first pin-holding assembly may be locked to the rod, optionally at a selectable orientation about the rod. A second pin-holding assembly may be slidably coupled to the rod. The first nut may be located between the assemblies, if the first nut will be turned to drive distraction, or the second assembly may be located between the first nut and the first assembly, if the first nut will be turned to drive compression. A second nut may be coupled to the rod. When the apparatus is fully assembled, the second assembly is between the nuts. The nuts may be used to engage the second assembly at opposite ends of its slidable base, to lock the second assembly to the rod during installation of an implant.

The apparatus may be locked to each of the pins. For example, a tube of each assembly may be mated with a protruding section of a corresponding pin and then locked to the pin. This mating may be performed while the assembly is in an adjustable configuration that permits the orientation of the tube to be changed in one or more planes, to enable coaxially aligning the tube with the pin. The pin then may be locked to the tube by adjusting a set screw of the assembly. The assembly may be adjusted via a user interface to a fixed configuration in which the orientation of the tube is fixed. An outrigger as disclosed herein may be mounted to and removed from the rod at any suitable times.

One of the nuts may be rotated to drive the second assembly along the rod. The nut may be rotated to cause threaded advancement of the nut against the second assembly. Once the desired amount of distraction or compression of bone has been achieved, the nuts may be used to engage the second assembly at both ends, to lock the second assembly to the rod.

A fixation device may be attached to at least one of the selected bones, optionally with the fixation device spanning the discontinuity. Exemplary fixation devices that may be suitable include bone plates, intramedullary nails, pins, screws, cables/wires, or the like.

The apparatus may be removed. The apparatus may be disconnected from each of the pins by loosening set screws of the first and second assemblies, and sliding the tubes of the assemblies off the pins. This process may be facilitated by first placing each assembly in an adjustable configuration.

The apparatus may be disassembled, sterilized, and reused. The first and second assemblies and the nuts may be removed from the rod. The apparatus components may be cleaned and placed into a container for sterilization.

VIII. System Configurations and Components

The apparatus may be provided by a system including any suitable combination of the following: (1) a rod, (2) a first assembly, (3) a second assembly, (4) at least one nut or at least a pair of nuts configured to be engaged with an external thread of the rod, (5) an outrigger that clamps to the rod, (6) one or more accessories for attachment to the outrigger (e.g., to an arm thereof), such as a joint alignment guide, a clamp, a tissue spreader, or the like, (7) a rod extension to increase the effective length of the rod, and/or (8) pins for insertion into bone, among others. Each of (1) through (8) may have any suitable combination of the features disclosed herein. At least one of the first assembly and the second assembly may be provided in a fully assembled form, optionally with no removable parts.

Any suitable combination of the system components may be housed in a container. The container may be configured to be resistant to heat, to permit the container and its contents to be sterilized by autoclaving. Any or all of components (1) through (8) above may be separate from one another in the container, to permit an apparatus to be assembled from separate components in the operating room. In some embodiments, the rod, the first assembly, the second assembly, and a pair of nuts may be provided as five separate components that can be assembled with one another to provide an apparatus capable of use with a pair of pins to distract and/or compress bone.

IX. Selected Embodiments

The following selected embodiments of the present disclosure are presented as a series of indexed paragraphs. These embodiments may be combined with one another and/or with any other suitable elements, features, or aspects of the present disclosure. The embodiments are included for illustration and are not intended to limit or define the entire scope of the invention.

Paragraph A1. An apparatus for distraction/compression of bone, comprising: (i) a rod having an external thread; (ii) a first assembly and a second assembly each coupled, or configured to be coupled, to the rod, and each configured to be attached to a respective pin extending into bone; and a nut engaged, or configured to be engaged, with the external thread and configured to be turned to drive the second assembly along the rod.

Paragraph A2. The apparatus of paragraph A1, wherein at least one of the first assembly and the second assembly includes a coupling portion defining a pin-receiving axis, wherein the coupling portion is connected to a base that interfaces, or is configured to interface, with the rod, and wherein the coupling portion has an adjustable configuration in which an orientation of the pin-receiving axis with respect to the base is adjustable in each plane of a pair of non-parallel planes and also has a fixed configuration in which the orientation is fixed.

Paragraph A3. The apparatus of paragraph A2, wherein the coupling portion is configured to be changed between the adjustable configuration and the fixed configuration by manipulating a single graspable member of the coupling portion.

Paragraph A4. The apparatus of paragraph A3, wherein the coupling portion is configured to be changed between the adjustable configuration and the fixed configuration by rotating the single graspable member of the coupling portion about an axis.

Paragraph A5. The apparatus of paragraph A4, wherein the single graspable member includes a winged member.

Paragraph A6. The apparatus of any of paragraphs A2 to A5, wherein the coupling portion includes a clamp configured to grip a section of the base in the fixed configuration of the coupling portion such that the clamp is locked to the base.

Paragraph A7. The apparatus of paragraph A6, wherein the base includes a sleeve through which the rod is configured to extend, and wherein the section of the base gripped by the clamp, and the sleeve, define respective parallel axes that are spaced from one another.

Paragraph A8. The apparatus of paragraph A6 or A7, wherein the clamp includes a pair of jaws that are connected to one another in a connection region of the clamp, wherein the coupling portion includes a fastening assembly that is adjustable to urge the jaws toward one another, and wherein the section of the base gripped by the clamp is located intermediate the connection region and the fastening assembly.

Paragraph A9. The apparatus of any of paragraphs A2 to A8, wherein the pair of non-parallel planes are orthogonal to one another.

Paragraph A10. The apparatus of paragraph A9, wherein the pair of non-parallel planes are respectively parallel and orthogonal to a long axis of the rod.

Paragraph A11. The apparatus of any of paragraphs A1 to A10, wherein each of the rod and the second assembly has at least one anti-rotation feature, and wherein the at least one anti-rotation feature of the rod is configured to interact with the at least one anti-rotation feature of the second assembly to permit axial travel of the second assembly along the rod over the external thread while preventing rotation of the second assembly about the rod.

Paragraph A12. The apparatus of paragraph A11, wherein the at least one anti-rotation feature of the rod includes a slot elongated along the rod and intersecting the external thread, and wherein the at least one anti-rotation feature of second assembly includes a projecting member positioned, or configured to be positioned, at least partially in the slot.

Paragraph A13. The apparatus of paragraph A11, wherein the at least one anti-rotation feature of the rod includes an axial flat intersecting the external thread.

Paragraph A14. The apparatus of paragraph A13, wherein the at least one anti-rotation feature of the rod includes a pair of axial flats intersecting the external thread and offset from one another about a long axis of the rod.

Paragraph A15. The apparatus of paragraph A14, wherein the pair of axial flats are offset from one another by 180 degrees about the long axis of the rod.

Paragraph A16. The apparatus of any of paragraphs A13 to A15, wherein the at least one anti-rotation feature of the second assembly includes a flat configured to face an axial flat of the rod.

Paragraph A17. The apparatus of any of paragraphs A11 to A16, wherein the external thread has a root, and wherein a bottom surface region of an anti-rotation feature of the at least one anti-rotation feature of the rod is closer than the root to a long axis of the rod.

Paragraph A18. The apparatus of any of paragraphs A11 to A17, wherein the external thread has a root, and wherein the root is closer than a bottom surface region of an anti-rotation feature of the at least one anti-rotation feature of the rod to a long axis of the rod.

Paragraph A19. The apparatus of any of paragraphs A11 to A18, wherein each anti-rotation feature of the at least one anti-rotation feature of the rod extends along a majority of the length of the rod.

Paragraph A20. The apparatus of any of paragraphs A11 to A19, wherein the external thread has an axial extent along the rod between opposite ends of the external thread, and wherein each anti-rotation feature of the at least one anti-rotation feature of the rod extends along at least a majority of the axial extent.

Paragraph A21. The apparatus of any of paragraphs A11 to A20, wherein the external thread defines a helical path extending between opposite ends of the thread, and wherein each anti-rotation feature of the at least one anti-rotation feature of the rod intersects the external thread on each revolution of a majority of revolutions of the helical path.

Paragraph A22. The apparatus of any of paragraphs A1 to A21, wherein the second assembly includes a sleeve, and wherein the rod extends, or is configured to extend, through the sleeve.

Paragraph A23. The apparatus of paragraph A22, wherein an anti-rotation feature of the at least one anti-rotation feature of the second assembly is formed integrally with the sleeve.

Paragraph A24. The apparatus of paragraph A22, wherein an anti-rotation feature of the at least one anti-rotation feature of the second assembly is formed separately from the sleeve.

Paragraph A25. The apparatus of any of paragraphs A22 to A24, wherein the nut is configured to be in contact with the sleeve as the nut is turned, to drive an anti-rotation feature of the at least one anti-rotation feature of the second assembly along an anti-rotation feature of the at least one anti-rotation feature of the rod.

Paragraph A26. The apparatus of any of paragraphs A1 to A25, wherein each of the first assembly and the second assembly has no removable parts.

Paragraph A27. The apparatus of any of paragraphs A1 to A26, wherein the nut is a first nut, further comprising a second nut engaged, or configured to be engaged, with the external thread of the rod.

Paragraph A28. The apparatus of any of paragraphs A1 to A27, wherein the first assembly is configured to be locked to the rod in only a finite plurality of predefined rotational positions about a long axis of the rod.

Paragraph A29. The apparatus of paragraph A28, wherein the predefined rotational positions are offset from one another by 360/n degrees, with n having an integer value.

Paragraph A30. The apparatus of paragraph A28 or A29, wherein the second assembly is coupled, or configured to be coupled, to the rod with a predefined rotational position matching one of the predefined rotational positions for the first assembly.

Paragraph A31. The apparatus of any of paragraphs A28 to A30, wherein the rod and the first assembly define respective mating structures, wherein the mating structures are configured to be fitted together in rotationally different configurations corresponding to the finite plurality of predefined rotational positions, and wherein each rotationally different configuration prevents rotation of the rod and the first assembly relative to one another about the long axis of the rod.

Paragraph A32. The apparatus of any of paragraphs A28 to A31, wherein the first assembly includes a movable locking member configured to prevent removal of the first assembly from the rod.

Paragraph A33. The apparatus of paragraph A32, wherein the locking member is configured to be manipulated to permit removal of the first assembly from the rod.

Paragraph A34. The apparatus of paragraph A32 or A33, wherein the locking member is biased toward a securing configuration, and wherein the locking member is configured to be changed to a releasing configuration that permits moving the first assembly to a different one of the rotational positions.

Paragraph A35. The apparatus of any of paragraphs A32 to A34, wherein the locking member is biased toward a securing configuration, and wherein the locking member is configured to be moved, optionally manually without the use of a tool, to a releasing configuration that permits axial removal of the first assembly from the rod.

Paragraph A36. The apparatus of any of paragraphs A32 to A35, wherein the first assembly includes a sleeve through which the rod is configured to extend, and wherein the locking member is movably connected to and supported by the sleeve.

Paragraph A37. The apparatus of any of paragraphs A1 to A36, wherein each of the first assembly and the second assembly includes a tube configured to receive the respective pin and has a set screw configured to lock the respective pin to the tube.

Paragraph A38. The apparatus of any of paragraphs A1 to A37, wherein the nut is configured to be adjustable between (a) a slidable configuration in which the nut is movable over the external thread parallel to a long axis of the rod, and (b) a rotatable configuration in which the nut is engaged with the external thread.

Paragraph A39. The apparatus of paragraph A38, wherein the nut includes a body and a securing member movably coupled to one another, and wherein the securing member has a surface region that is complementary to a portion of the external thread.

Paragraph A40. The apparatus of paragraph A39, wherein the securing member is movable with respect to the body between a deployed configuration for engagement of the securing member with the external thread and a retracted configuration that permits the nut to slide axially along the rod over the external thread.

Paragraph A41. The apparatus of paragraph A40, wherein the securing member is biased toward the deployed configuration.

Paragraph A42. The apparatus of any of paragraphs A1 to A41, wherein the nut includes a body and a securing member coupled to one another, and wherein the securing member is movable with respect to the body between a deployed configuration for engagement of the securing member with the external thread and a retracted configuration that permits the nut to slide axially along the rod over the external thread.

Paragraph A43. The apparatus of paragraph A42, wherein the securing member defines one or more grooves that are complementary to one or more corresponding lengths of the external thread.

Paragraph A44. The apparatus of paragraph A42 or A43, wherein the body defines an aperture having a central through-axis, wherein a surface region of the securing member is complementary to a portion of the external thread, and wherein the surface region of the securing member is closer to the through-axis in the deployed configuration than the retracted configuration.

Paragraph A45. The apparatus of any of paragraphs A42 to A44, wherein nut includes a spring that biases the securing member toward the deployed configuration.

Paragraph A46. The apparatus of paragraph A45, wherein the securing member is configured to be moved from the deployed configuration to the retracted configuration by pressing the securing member.

Paragraph A47. The apparatus of any of paragraphs A42 to A46, wherein the nut includes at least three wings.

Paragraph A48. The apparatus of any of paragraphs A1 to A47, wherein at least one of the first assembly and the second assembly includes at least one leg and a tube, wherein the tube is connected, or configured to be connected, to the rod via the at least one leg and to receive one of the pins, and wherein an outside diameter of the tube matches a diameter of the at least one leg.

Paragraph A49. The apparatus of any of paragraphs A1 to A48, wherein the second assembly has a base including a pair of legs connected to one another with a sleeve through which the rod extends or is configured to extend.

Paragraph A50. The apparatus of paragraph A49, wherein the base includes a bridge connecting the legs and located opposite the sleeve.

Paragraph A51. The apparatus of any of paragraphs A1 to A50, further comprising a third assembly including a clamp configured to mount the third assembly to the rod, wherein the clamp is configured to engage the external thread such that the clamp is locked to the rod.

Paragraph A52. The apparatus of paragraph A51, wherein jaws of the clamp form a mouth that is adjustable to be larger than a diameter of the external thread, such that the rod can be placed between the jaws by moving the rod and the clamp relative to one another orthogonal to a long axis of the rod.

Paragraph A53. The apparatus of paragraph A51 or A52, wherein the clamp defines one or more grooves that are complementary to a portion of the external thread.

Paragraph A54. The apparatus of any of paragraphs A51 to A53, wherein the external thread of the rod has a crest between a pair of flanks, and wherein at least one jaw of the clamp is configured to preferentially engage at least one of the flanks relative to the crest when the clamp is locked to the rod.

Paragraph A55. The apparatus of any of paragraphs A51 to A54, wherein the third assembly includes an arm defining an arm axis, wherein the clamp defines a through-axis, and wherein the third assembly is configured such that (a) an orientation of the arm axis is adjustable in a plane parallel to the through-axis, after the rod is disposed between jaws of the clamp and before the clamp is locked to the rod, and (b) the orientation is fixed when the clamp is locked to the rod.

Paragraph A56. The apparatus of any of paragraphs A51 to A55, wherein the clamp is a first clamp, further comprising a second clamp mounted, or configured to be mounted, to an arm of the third assembly and configured to be locked to a third pin extending into bone.

Paragraph A57. The apparatus of any of paragraphs A1 to A56, wherein the first assembly is already coupled to the rod, optionally firmly and/or non-removably attached to the rod.

Paragraph B. A method of distracting/compressing bone performed with the apparatus of any of paragraphs A1 to A56, the method comprising in any order: (1) driving a first pin and a second pin into a skeleton of a subject; (2) attaching the first assembly to the first pin and the second assembly to the second pin; and (3) turning the nut to drive the second assembly along the rod.

Paragraph C. A method of distracting/compressing bone performed with the apparatus of any of paragraphs A1 to A57, the method comprising in any order: (1) driving a first pin and a second pin into a skeleton of a subject; (2) attaching the first assembly to the first pin and the second assembly to the second pin; and (3) turning the nut to drive the second assembly along the rod.

Paragraph D. A method of assembling the apparatus of any of paragraphs A1 to A57, the method comprising in any order: (1) coupling the first assembly and/or the second assembly to the rod; and (2) engaging the nut with the external thread of the rod.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. An apparatus for distraction/compression of bone, comprising:
    a rod having an external thread;
    a first assembly and a second assembly each coupled, or configured to be coupled, to the rod, and each configured to be attached to a respective pin extending into bone; and
    a nut engaged, or configured to be engaged, with the external thread and configured to be turned to drive the second assembly along the rod;
    wherein at least one of the first assembly and the second assembly includes a coupling portion defining a pin-receiving axis, wherein each respective coupling portion is connected to a base that interfaces, or is configured to interface, with the rod, wherein each respective coupling portion has an adjustable configuration in which an orientation of the pin-receiving axis with respect to the base is adjustable in each plane of a pair of non-parallel planes and also has a fixed configuration in which the orientation is fixed, wherein each respective coupling portion is configured to be changed between the adjustable configuration and the fixed configuration by rotating a single graspable member of the respective coupling portion about an axis, and wherein each respective coupling portion includes a clamp configured to grip a section of the base in the fixed configuration of the respective coupling portion such that the clamp is locked to the base.

2. The apparatus of claim 1, wherein the base of each respective coupling portion includes a sleeve through which the rod extends, or is configured to extend, and wherein, for each respective coupling portion, the section of the base gripped by the clamp and the sleeve define respective parallel axes that are spaced from one another.

3. The apparatus of claim 1, wherein the clamp of each respective coupling portion includes a pair of jaws that are connected to one another in a connection region of the clamp, wherein each respective coupling portion includes a fastening assembly that is adjustable to urge the jaws toward one another, and wherein, for each respective coupling portion, the section of the base gripped by the clamp is located intermediate the connection region and the fastening assembly.

4. The apparatus of claim 1, wherein the pair of non-parallel planes are respectively parallel and orthogonal to a long axis of the rod.

5. An apparatus for distraction/compression of bone, comprising:
a rod having an external thread;
a first assembly and a second assembly each coupled, or configured to be coupled, to the rod, and each configured to be attached to a respective pin extending into bone; and
a nut engaged, or configured to be engaged, with the external thread and configured to be turned to drive the second assembly along the rod;
wherein each of the rod and the second assembly has at least one anti-rotation feature, and wherein the at least one anti-rotation feature of the rod is configured to interact with the at least one anti-rotation feature of the second assembly to permit axial travel of the second assembly along the rod while preventing rotation of the second assembly about the rod, and
wherein the first assembly is configured to be locked to the rod at a plurality of rotational positions about a long axis of the rod.

6. The apparatus of claim 5, wherein the at least one anti-rotation feature of the rod includes a slot elongated along the rod and intersecting the external thread, and wherein the at least one anti-rotation feature of the second assembly includes a projecting member positioned, or configured to be positioned, at least partially in the slot.

7. The apparatus of claim 5, wherein the at least one anti-rotation feature of the rod includes an axial flat intersecting the external thread.

8. The apparatus of claim 5, wherein the first assembly is configured to be locked to the rod in only a finite plurality of predefined rotational positions about the long axis of the rod.

9. The apparatus of claim 8, wherein the rod and the first assembly define respective mating structures, wherein the mating structures are configured to be fitted together in rotationally different configurations corresponding to the finite plurality of predefined rotational positions, and wherein each rotationally different configuration prevents rotation of the rod and the first assembly relative to one another about the long axis of the rod.

10. The apparatus of claim 8, wherein the first assembly includes a locking member configured to prevent removal of the first assembly from the rod.

11. The apparatus of claim 10, wherein the locking member is biased toward a securing configuration, and wherein the locking member is configured to be changed to a releasing configuration that permits moving the first assembly to a different one of the rotational positions.

12. The apparatus of claim 5, wherein the second assembly includes a sleeve, wherein the rod extends, or is configured to extend, through the sleeve, and wherein the at least one anti-rotation feature of the second assembly is formed integrally with the sleeve or mounted to the sleeve.

13. The apparatus of claim 5, wherein at least one of the first assembly and the second assembly includes a coupling portion defining a pin-receiving axis, wherein each respective coupling portion is connected to a base that interfaces, or is configured to interface, with the rod, wherein each respective coupling portion has an adjustable configuration in which an orientation of the pin-receiving axis with respect to the base is adjustable in each plane of a pair of non-parallel planes and also has a fixed configuration in which the orientation is fixed, and wherein each respective coupling portion is configured to be changed between the adjustable configuration and the fixed configuration by manipulating a single graspable member of the respective coupling portion.

14. The apparatus of claim 13, wherein each respective coupling portion is configured to be changed between the adjustable configuration and the fixed configuration by rotating the single graspable member of the respective coupling portion about an axis.

15. The apparatus of claim 5, wherein each of the first assembly and the second assembly has no removable parts.

16. An apparatus for distraction/compression of bone, comprising:
a rod having an external thread;
a first assembly and a second assembly each coupled, or configured to be coupled, to the rod, and each configured to be attached to a respective pin extending into bone; and
a nut engaged, or configured to be engaged, with the external thread and configured to be turned to drive the second assembly along the rod;
wherein the nut is configured to be adjustable between (a) a slidable configuration in which the nut is movable over the external thread parallel to a long axis of the rod, and (b) a rotatable configuration in which the nut is engaged with the external thread.

17. The apparatus of claim 16, wherein the nut includes a body and a securing member movably coupled to one another, and wherein the securing member has a surface region that is complementary to a portion of the external thread.

18. The apparatus of claim 17, wherein the securing member is movable with respect to the body between a deployed configuration for engagement of the securing member with the external thread and a retracted configuration that permits the nut to slide axially along the rod over the external thread.

19. The apparatus of claim 18, wherein the securing member is biased toward the deployed configuration.

* * * * *